(12) United States Patent
Suzuki et al.

(10) Patent No.: US 7,608,046 B2
(45) Date of Patent: Oct. 27, 2009

(54) APPARATUS FOR AND METHOD OF BIOTIC SLEEP STATE DETERMINING

(75) Inventors: Takuji Suzuki, Tokyo (JP); Kenichi Kameyama, Tokyo (JP); Kazushige Ouchi, Tokyo (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 11/866,160

(22) Filed: Oct. 2, 2007

(65) Prior Publication Data

US 2008/0027331 A1 Jan. 31, 2008

Related U.S. Application Data

(63) Continuation of application No. 11/045,281, filed on Jan. 31, 2005, now Pat. No. 7,351,206.

(30) Foreign Application Priority Data

Mar. 30, 2004 (JP) ............................. 2004-101397

(51) Int. Cl.
*A61B 5/00* (2006.01)
(52) U.S. Cl. ....................... 600/500; 600/485
(58) Field of Classification Search ........................ None
See application file for complete search history.

(56) References Cited

U.S. PATENT DOCUMENTS

| 5,902,250 A | 5/1999 | Verrier et al. |
| 6,569,094 B2 | 5/2003 | Suzuki et al. |
| 6,607,484 B2 * | 8/2003 | Suzuki et al. ............... 600/300 |
| 2008/0027331 A1 | 1/2008 | Suzuki et al. |

FOREIGN PATENT DOCUMENTS

| JP | 6-217946 | 8/1994 |
| JP | 7-143972 | 6/1995 |

(Continued)

OTHER PUBLICATIONS

U.S. Appl. No. 12/167,586, filed Jul. 3, 2008, Ouchi, et al.

(Continued)

*Primary Examiner*—Robert L Nasser
(74) *Attorney, Agent, or Firm*—Oblon, Spivak, McClelland, Maier & Neustadt, L.L.P.

(57) ABSTRACT

A biotic sleep state determining apparatus that determines a sleep state of a subject based on a series of pulse interval data that indicate a time interval of one cycle of a pulse wave of the subject, and on body movement data that indicates a body movement of the subject, the apparatus includes a body movement determining unit that determines that the body movement occurs if a fluctuation amount of the body movement data is greater than a first predetermined threshold, a pulse interval data processor that processes the series of pulse interval data after removing pulse interval data measured in parallel with the body movement data from the series of pulse interval data, if the body movement determining unit determines that the body movement occurs, and a sleep state determining unit that determines the sleep state based on autonomic nerve indexes acquired from the series of pulse interval data processed by the pulse interval data processor.

5 Claims, 16 Drawing Sheets

FOREIGN PATENT DOCUMENTS

| | | |
|---|---|---|
| JP | 8-299292 | 11/1996 |
| JP | 2000-215 | 1/2000 |
| JP | 2001-204694 | 7/2001 |
| JP | 2001-327482 | 11/2001 |
| JP | 2002-34955 | 2/2002 |
| JP | 2002-219116 * | 8/2002 |
| JP | 2002-291710 | 10/2002 |
| JP | 2003-240320 | 8/2003 |

OTHER PUBLICATIONS

U.S. Appl. No. 12/208,769, filed Sep. 11, 2008, Yokoyama, et al.

* cited by examiner

| TIME | PULSE INTERVAL(s) | |
|---|---|---|
| 23 : 30 : 00.0045 | 0.9845 | |
| 23 : 30 : 01.0090 | 1.0045 | |
| 23 : 32 : 01.9990 | 0.9900 | |
| ⋮ | ⋮ | |
| 24 : 30 : 00.0045 | 0.9845 | |
| ~~24 : 30 : 01.0090~~ | ~~1.0045~~ | ← REMOVED BECAUSE OF BODY MOVEMENT |
| 24 : 32 : 01.9990 | 0.9900 | |
| ⋮ | ⋮ | |
| 24 : 50 : 00.0045 | 0.9845 | |
| ~~24 : 50 : 01.0090~~ | ~~1.0045~~ | ← REMOVED BECAUSE OF WAVEFORM ABNORMALITY |
| 24 : 52 : 01.9990 | 0.9900 | |

APPARATUS FOR AND METHOD OF BIOTIC SLEEP STATE DETERMINING

CROSS-REFERENCE TO RELATED APPLICATIONS

This application is a Continuation of and claims the benefit of priority under 35 U.S.C § 120 from U.S. Ser. No. 11/045,281, filed Jan. 31, 2005 now U.S. Pat. No. 7,351,206, and claims the benefit of priority under 35 U.S.C. § 119 from Japanese Patent Application No. 2004-101397, filed Mar. 30, 2004, the entire contents of each which are incorporated herein by reference.

BACKGROUND OF THE INVENTION

1) Field of the Invention

The present invention relates to a technology for determining a biotic sleep state.

2) Description of the Related Art

There is conventionally known a biotic sleep state determining apparatus that determines a sleep state of a subject based on pulse interval data which is data on one cycle of a pulse wave of the subject, and on body movement data which indicates a body movement of the subject. This sleep state determining apparatus attracts attention as one that can determine a sleep state handy in an ordinary life, as compared with a complicated apparatus, referred to as "polysomnogram", that determines a sleep state from biological signal patterns such as brain waves, eye movement, an electrical activity of muscles, and an electrical activity of a heart.

In this sleep state determining apparatus, a beat interval of heartbeat that is an activity of an autonomic nerve during sleep is regarded as a pulse interval of a pulse wave, and the sleep state is determined based on autonomic nerve indexes acquired from a fluctuation in the pulse interval. For example, a pulse wave that is a bloodstream fluctuation of a blood vessel of a hand fluctuates synchronously with the heartbeat, so that the beat interval of the heartbeat can be acquired from the pulse interval of the pulse wave. According to conventional techniques disclosed in, for example, Japanese Patent Application Laid-Open (JP-A) No. 2002-291710 and JP-A No. H07-143972, the sleep state is determined based on autonomic nerve indexes acquired from frequency spectrum components of pulse wave data. That is, a series of pulse interval data are acquired from the pulse wave data, and the pulse interval data is converted into a frequency spectrum distribution. The autonomic nerve indexes are acquired from power spectra in a low-frequency region (near 0.05 to 0.15 hertz) and a high-frequency region (near 0.15 to 0.4 hertz) obtained from the series of pulse interval data converted into the frequency spectrum distribution. The sleep state is determined based on the acquired autonomic nerve indexes. According to a conventional technique disclosed in JP-A No. 2002-34955, not only pulse wave data but also body movement data are measured, so as to determine a sleep state as to whether the subject is in a state of awakening, rapid eye movement (REM) sleep, non-rapid eye movement (NREM) sleep, or a difficulty in remaining asleep through the night (intermediate arousal).

The conventional techniques disclosed in the above applications have, however, the following disadvantages. Although the sleep state such as the state of awakening, REM sleep, NREM sleep, or intermediate arousal can be determined, the determination tends to be influenced by a body movement such as movement of the limbs and suffers low determination accuracy for determining the sleep state. This is because the pulse wave data is obtained by measuring pulse waves that are bloodstream fluctuations of the blood vessel of the hand. In addition, the pulse wave data tends to be influenced by a pulse wave abnormality such as arrhythmia or apnea, and suffers the low determination accuracy.

SUMMARY OF THE INVENTION

It is an object of the present invention to solve at least the problems in the conventional technology.

A biotic sleep state determining apparatus according to one aspect of the present invention, that determines a sleep state of a subject based on a series of pulse interval data that indicate a time interval of one cycle of a pulse wave of the subject, and on body movement data that indicates a body movement of the subject, includes a body movement determining unit that determines that the body movement occurs if a fluctuation amount of the body movement data is greater than a first predetermined threshold, a pulse interval data processor that processes the series of pulse interval data after removing pulse interval data measured in parallel with the body movement data from the series of pulse interval data, if the body movement determining unit determines that the body movement occurs, and a sleep state determining unit that determines the sleep state based on autonomic nerve indexes acquired from the series of pulse interval data processed by the pulse interval data processor.

A biotic sleep state determining method according to another aspect of the present invention of determining a sleep state of a subject based on a series of pulse interval data that indicate a time interval of one cycle of a pulse wave of the subject, and on body movement data that indicates a body movement of the subject, includes determining that the body movement occurs if a fluctuation amount of the body movement data is greater than a first predetermined threshold, processing the series of pulse interval data after removing pulse interval data measured in parallel with the body movement data from the series of pulse interval data, if the body movement occurs, and determining the sleep state based on autonomic nerve indexes acquired from the series of pulse interval data processed.

DETAILED DESCRIPTIONS

Exemplary embodiments of a sleep state determining apparatus according to the present invention will be explained hereinafter in detail with reference to the accompanying drawings. However, it should be noted that the present invention is not limited by these embodiments.

In the first embodiment, the sleep state determining apparatus is applied to lessen the influence of a body movement on a pulse wave sensor using an acceleration sensor. In the second embodiment, the sleep state determining apparatus is applied to detect an abnormality such as arrhythmia or apnea during sleep. In the third embodiment, the sleep state determining apparatus is applied to an instance of using a mat sensor as a body movement sensor. In the fourth embodiment, the sleep state determining apparatus is applied to an instance of using a mat sensor as a body movement sensor and a pulse wave sensor.

Figure 1:
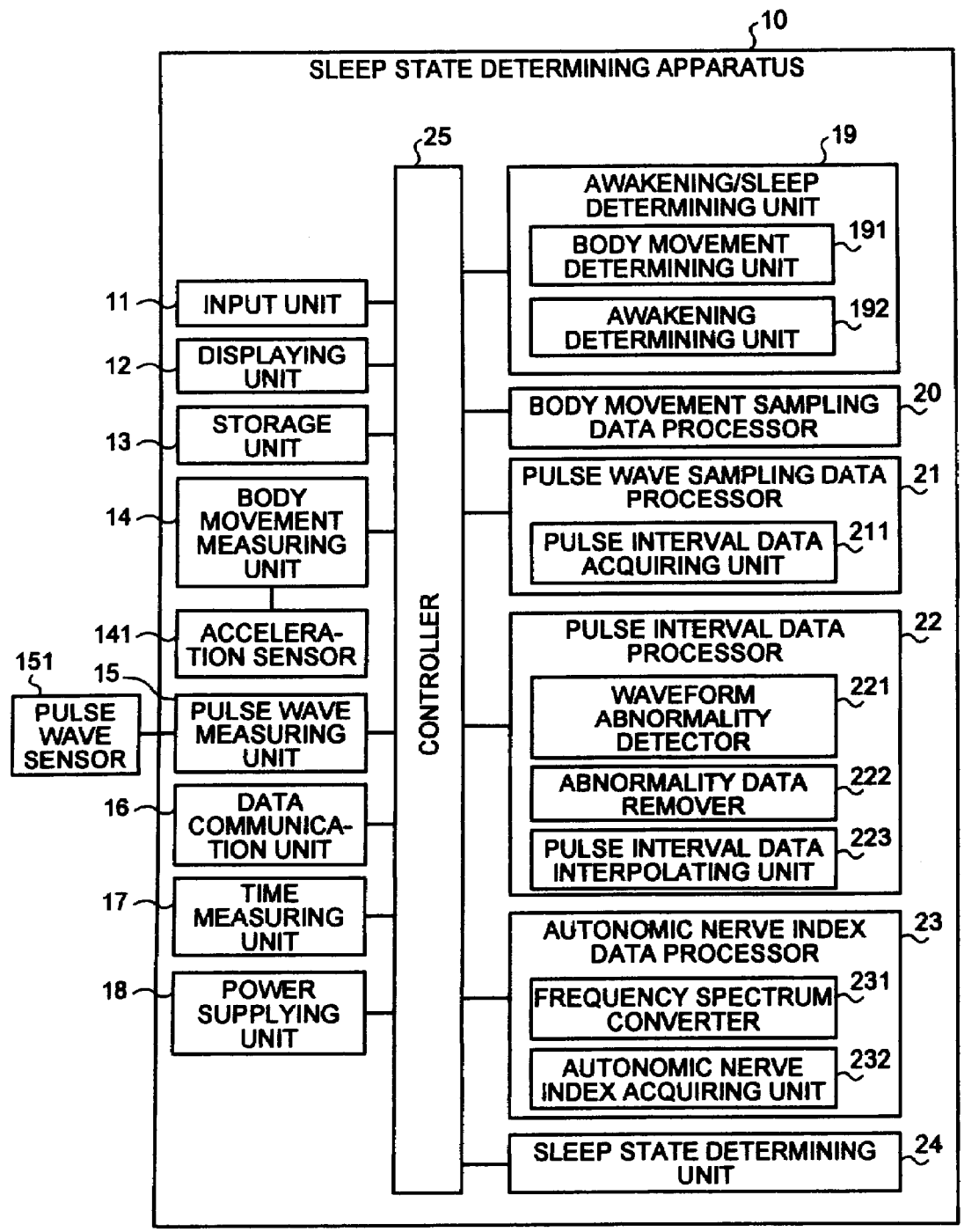
FIG. 1 is a functional block diagram of configuration of a sleep state determining apparatus according to a first embodiment of the present invention.

In the first embodiment, the instance in which the sleep state determining apparatus lessens the influence of the body movement on the pulse wave sensor using the acceleration sensor will be explained. Configuration of the sleep state determining apparatus according to the present invention will first be explained. FIG. 1 is a functional block diagram of the configuration of the sleep state determining apparatus according to the first embodiment of the present invention. The sleep state determining apparatus 10 includes an input unit 11, a displaying unit 12, a storage unit 13, a body movement measuring unit 14, a pulse wave measuring unit 15, a data communication unit 16, a time measuring unit 17, a power supplying unit 18, an awakening/sleep determining unit 19, a body movement sampling data processor 20, a pulse wave sampling data processor 21, a pulse interval data processor 22, an autonomic nerve index data processor 23, a sleep state determining unit 24, and a controller 25.

Figure 2:
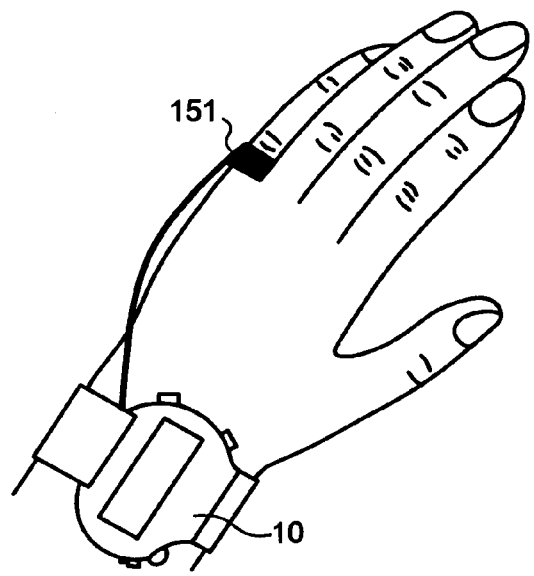
FIG. 2 is one example of attachment of the sleep state determining apparatus.
Figure 3:
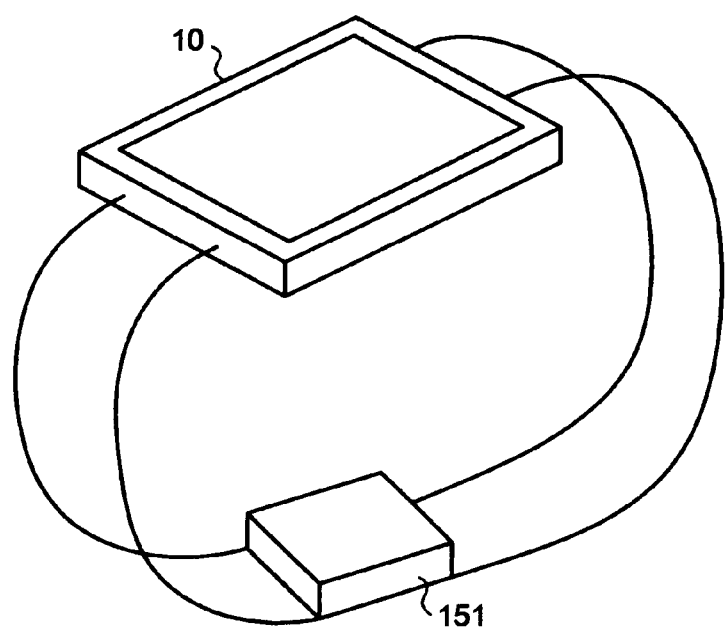
FIG. 3 is another example of attachment of the sleep state determining apparatus.

One example of attachment of the sleep state determining apparatus 10 shown in FIG. 1 will be explained with reference to FIGS. 2 and 3. In FIG. 2, a pulse wave sensor 151 is attached to a finger and the sleep state determining apparatus 10 is attached to a wrist like a wristwatch. Alternatively, the pulse wave sensor 151 may be attached to the palm of a hand using a sticking plaster. Further, as shown in FIG. 3, the pulse wave sensor 151 using an infrared light emitting diode (LED) or a red LED, and the sleep state determining apparatus 10 can be integrated with each other and attached onto an artery of the wrist.

In FIG. 1, the input unit 11 is a switch for allowing a user to turn a power ON or OFF or to issue a request or an instruction of display switching. The displaying unit 12 displays a sleep state determination result, and is, for example, a liquid crystal display (LCD). The storage unit 13 stores measurement data such as pulse wave data and body movement data, processed data such as pulse interval data, and data such as thresholds for determining a sleep state. Specifically, the storage unit 13 is a flash memory or the like.

The body movement measuring unit 14 measures acceleration data as body movement data that indicates a body movement of a subject, and performs data conversion. The body movement measuring unit 14 includes an acceleration sensor 141. The acceleration sensor 141 measures accelerations of −2 g to 2 g in three-axis directions, and is mounted in the sleep state determining apparatus 10. The body movement measuring unit 14 adjusts a gain and an offset of analog data measured by the acceleration sensor 141 using an adjustment circuit, converts the adjusted data into a digital quantity using a 10-bit analog-to-digital (A/D) converter, and inputs the digital quantity to the controller 25.

The pulse wave measuring unit 15 measures pulse wave data on the subject and converts the pulse wave data. The pulse wave measuring unit 15 includes a pulse wave sensor 151. The pulse wave sensor 151, which is composed by a blue LED and a photodiode, irradiates a light onto a surface of a finger skin, detects a fluctuation in a reflected light that changes according to a bloodstream fluctuation in a capillary using the photodiode, thereby measuring a pulse wave. The pulse wave measuring unit 15 converts an output current from the photodiode of the pulse sensor 151 into a voltage using a current-to-voltage converter. In addition, the pulse wave measuring unit 15 amplifies the voltage using an amplifier, performs filtering the amplified voltage using a highpass filter (with a cutoff frequency of 0.1 hertz) and a lowpass filter (with a cutoff frequency of 50 hertz), converts the filtered voltage into a digital quantity using a 10-bit A/D converter, and inputs the digital quantity to the controller 25.

The data communication unit 16 performs data communication with a personal computer or a personal digital assistant (PDA) terminal through a wireless local area network (LAN) or the like. Specifically, the data communication unit 16 is a unit according to Bluetooth™. The time measuring unit 17 measures a time. Specifically, the time measuring unit 17 is a real clock IC or the like. The power supplying unit 18 supplies a power to the sleep state determining apparatus 10. Specifically, the power supplying unit 18 is a battery.

The awakening/sleep determining unit 19 determines whether the subject awakes based on the body movement data on the subject. The awakening/sleep determining unit 19 includes a body movement determining unit 191 and an awakening determining unit 192. The body movement determining unit 191 determines that a body movement occurs if a fluctuation amount of the body movement data is greater than a first predetermined threshold. For example, as the first predetermined threshold, 0.01 G, which is a minimum value of minute body movement used in a body movement measuring instrument, is used. The awakening determining unit 192 determines that a body movement occurs during awakening if a frequency of occurrence of the body movement determined by the body movement determining unit 191 is equal to or greater than a second predetermined threshold. The awakening determining unit 192 also determines that a body movement occurs during sleeping if a frequency of occurrence of the body movement determined by the body movement determining unit 191 is smaller than a second predetermined threshold. If the body movement occurrence frequency determined by the body movement determining unit 191 is equal to or greater than the second predetermined threshold, and the pulse interval data is shorter than an average of past pulse interval data during sleep, the awakening determining unit 192 determines that the body movement occurs during awakening. For example, as the second predetermined threshold, a frequency of 20 times/minute is selected from among past body movement frequencies during awakening.

The body movement sampling data processor 20 differentiates the acceleration data in three-axis directions acquired from the body movement measuring unit 14 by time to thereby obtain differential coefficients of accelerations in the three-axis directions. In addition, the body movement sampling data processor 20 obtains a fluctuation amount of the body movement data, which is a square root of a sum of squares of the differential coefficients of the respective accelerations in the three-axis directions, and a body movement amount that is an average of a fluctuation amount of the body movement data within the pulse interval. The body movement sampling data processor 20 provides, as data for the body movement determination, the fluctuation amount of the body movement data and the body movement amount to the body movement determining unit 191.

The pulse wave sampling data processor 21 samples pulse wave data from pulse waves of the subject, and acquires the pulse interval data. The pulse wave sampling data processor 21 includes a pulse interval data acquiring unit 211 that acquires pulse interval data which is time interval data on one cycle of the pulse wave of the subject.

Specifically, the pulse interval data acquiring unit 211 samples pulse wave data from the pulse wave, differentiates a series of pulse wave data thus sampled by time, and removes direct-current fluctuation components from the series of pulse wave data. The pulse interval data acquiring unit 211 acquires maximum and minimum pulse wave data in a time interval of about one second before and after a processing point of the series of pulse wave data from which the direct-current fluctuation components are removed. In addition, the pulse interval data acquiring unit 211 sets a predetermined value between the maximum and the minimum as a third predetermined threshold. For example, as the third predetermined threshold, a value having an amplitude of a difference between the maximum and the minimum that is 90% of an amplitude of the minimum is used. Further, the pulse interval data acquiring unit 211 calculates periods of time when a series of pulse wave data coincident with the third predetermined threshold appear, from the series of pulse wave data, from which the direct-current fluctuation components are removed. In addition, the unit 211 acquires the pulse interval data from an interval of the calculated periods of time. A method of calculating the pulse interval data by the pulse interval data acquiring unit 211 shown in FIG. 1 will be explained more specifically with reference to FIG. 4.

Data in the series of pulse wave data just before the data exceeds the third predetermined threshold is assumed as y1, and a time when the data y1 appears is assumed as t1. Data in the series of pulse wave data just after the data exceeds the third predetermined threshold is assumed as y2, and a time when the data y2 appears is assumed as t2. Data in the series of pulse wave data coincident with the third predetermined threshold is assumed as y0, and a time when the data y0 appears is assumed as t. Based on this assumption, the time t when the data in the series of pulse wave data coincides with the third predetermined threshold is calculated by the following Equation 1.

$$t = t1 + (t2-t1) \times (y0-y1)/(y2-y1) \qquad (1)$$

Therefore, if the previous time when the data thus calculated in the series of pulse wave data coincident with the third predetermined threshold appears is t0, the pulse interval data is obtained as a time interval of (t−t0).

Referring back to FIG. 1, the pulse interval data processor 22 generates a series of pulse interval data from the pulse interval data acquired by the pulse wave sampling data processor 21, for example, a data set for one minutes, and processes the series of pulse interval data. The pulse interval data processor 22 includes a waveform abnormality detector 221, an abnormality data remover 222, and a pulse interval data interpolating unit 223. The waveform abnormality detector 221 determines that the amount of the body movement is large if the body movement determining unit 191 determines that the body movement occurs, and if the body movement amount of the body movement data for which it is determined that the body movement occurs, is equal to or greater than a fifth predetermined threshold. In addition, the waveform abnormality detector 221 detects the pulse interval data measured in parallel with the body movement data, for which it is determined that the body movement occurs during sleep, as a waveform abnormality. For example, as the fifth predetermined threshold, 1 G is used.

Figures 4, 5:
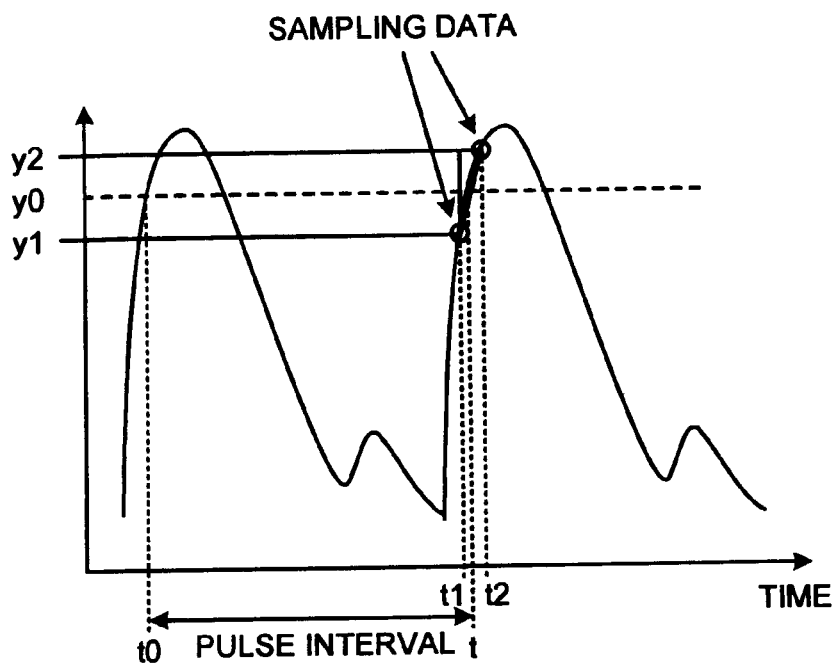
FIG. 4 is a calculation method of calculating pulse interval data by a pulse interval data acquiring unit.
FIG. 5 is one example of a series of pulse interval data, from which pulse interval data, for which it is determined that a body movement occurs, is removed, by an abnormal data remover.
Figure 6:
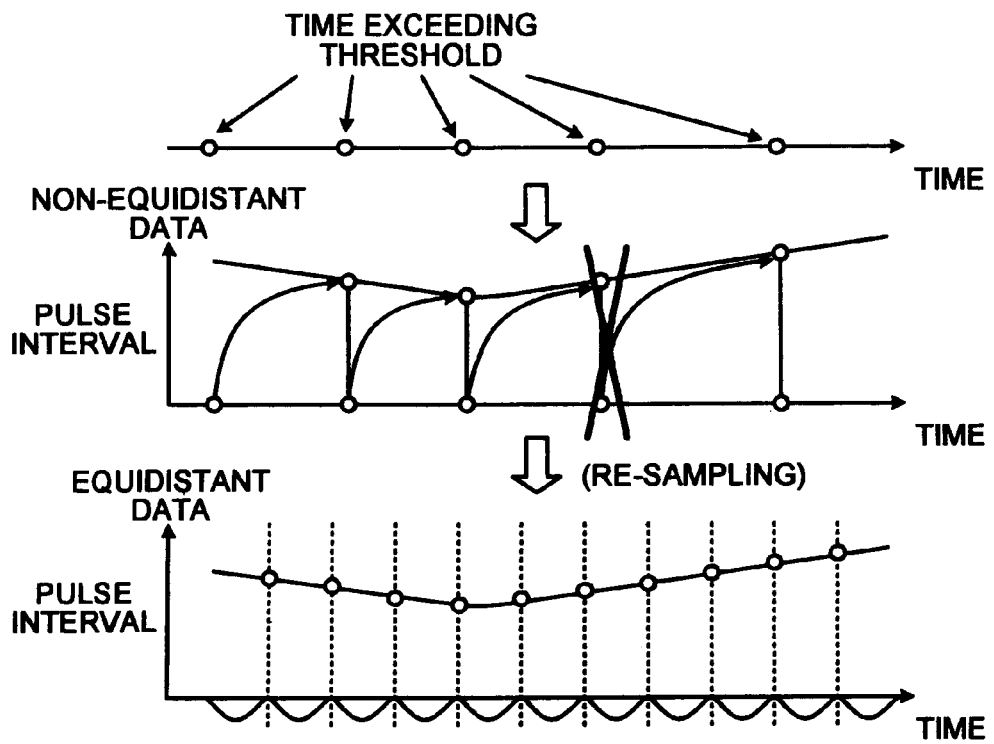
FIG. 6 is one example of interpolating the series of pulse interval data by a pulse interval data interpolating unit.

The abnormality data remover 222 is a processor that removes the pulse interval data detected as the waveform abnormality by the waveform abnormality detector 221 from the series of pulse interval data. The pulse interval data interpolating unit 223 is a processor that interpolates the series of pulse interval data, from which the pulse interval data detected as the waveform abnormality by the abnormality data remover 222 is removed, using a high-order polynomial. Specifically, one example of the series of pulse interval data from which the pulse interval data, for which it is determined that the body movement occurs, is removed by the abnormality data remover 222 shown in FIG. 1 will be explained. In addition, one example of interpolating the series of pulse interval data using the pulse interval data interpolating unit 223 shown in FIG. 1 will be explained. FIG. 5 is one example of the series of pulse interval data from which the pulse interval data, for which it is determined that the body movement occurs, is removed by the abnormality data remover 222 shown in FIG. 1. FIG. 6 is one example of interpolating the series of pulse interval data using the pulse interval data interpolating unit 223 shown in FIG. 1.

As shown in FIG. 5, the pulse interval data processed by the pulse interval data processor 22 is originally non-equidistant data and abnormality data caused by the body movement and the waveform abnormality is removed from the pulse interval data. Therefore, as shown in FIG. 6, the pulse interval data interpolating unit 223 interpolates and re-samples the non-equidistant pulse interval data, thereby generates equidistant pulse interval data. For example, the pulse interval data interpolating unit 223 generates the equidistant pulse interval data using three sampling points before and after a point at which the data is interpolated using cubic polynomial interpolation. After the pulse interval data processor 22 thus generates the equidistant pulse interval data from the series of non-equidistant pulse interval data, the autonomic nerve index data processor 23 converts the equidistant pulse interval data into the frequency spectrum distribution.

Referring back to FIG. 1, the autonomic nerve index data processor 23 acquires two autonomic nerve indexes, i.e., an index LF in a low frequency region (near 0.05 to 0.15 hertz) and an index HF in a high frequency region (near 0.15 to 0.4 hertz) for the sleep state determination. The autonomic nerve index data processor 23 includes a frequency spectrum converter 231 and an autonomic nerve index acquiring unit 232. The frequency spectrum converter 231 is a data processor that converts the series of pulse interval data processed by the pulse interval data processor 22 into the frequency spectrum distribution by an analysis method such as a fast Fourier transform (FFT) method. The autonomic nerve index acquiring unit 232 is a processor that acquires the autonomic nerve indexes LF and HF from a plurality of power spectra of the series of pulse interval data converted into the frequency spectrum distribution by the frequency spectrum converter 231. Specifically, the autonomic nerve index acquiring unit 232 acquires the autonomic nerve indexes LF and HF by averaging three points, i.e., a peak of the power spectra and two equidistant points before and after the peak.

Figure 7:
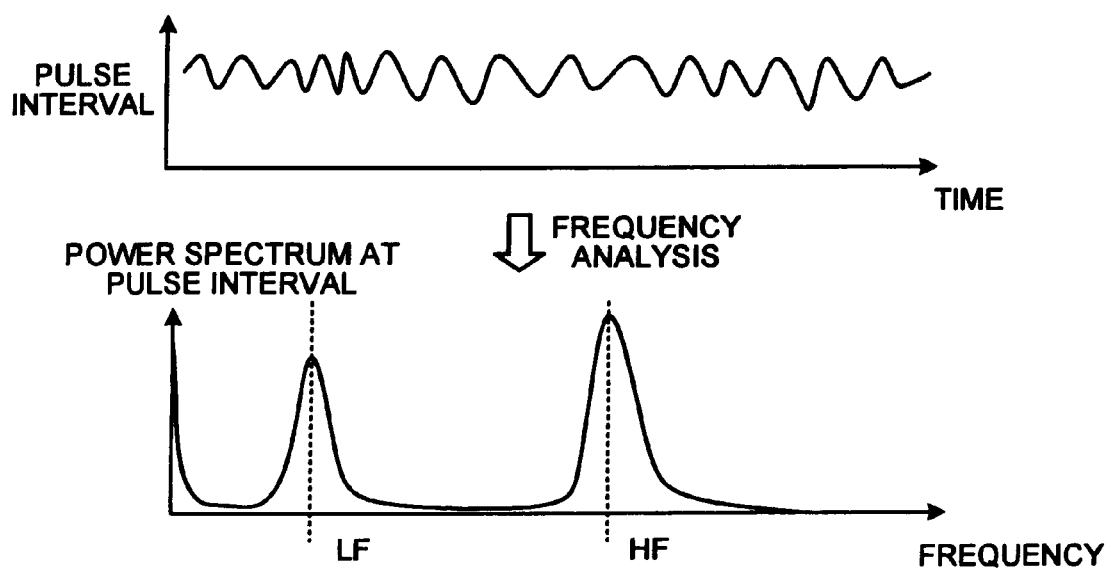
FIG. 7 is one example of acquiring autonomic nerve index from power spectra by an autonomic nerve index data processor.

One example of acquiring the autonomic nerve indexes LF and HF from the power spectra by the autonomic nerve index data processor 23 shown in FIG. 1 will be explained with reference to FIG. 7. When the pulse interval data processor 22 generates the equidistant pulse interval data, the autonomic nerve index data processor 23 performs a frequency analysis using the FFT method to convert the series of pulse interval data into the frequency spectrum distribution. While an autoregressive (AR) model, a maximum entropy method, a wavelet method or the like may be used as the frequency analysis method, the FFT method which imposes a lighter data processing burden is used in this embodiment.

In FIG. 1, the sleep state determining unit 24 determines the sleep state of the subject based on the index LF, which is the power spectrum in the low frequency region (near 0.05 to 0.15 hertz), and HF, which is the power spectrum in the high frequency region (near 0.15 to 0.4 hertz), respectively among the power spectra. Specifically, if LF/HF is smaller than a first determination threshold and HF is greater than a second determination threshold, the sleep state determining unit 24 determines that the subject is in a deep sleep state. If the LF/HF is greater than a third determination threshold, the index HF is smaller than a fourth determination threshold, and a sum of standard derivatives of the indexes LF and HF is greater than a fifth determination threshold, then the sleep state determining unit 24 determines that the subject is in a REM sleep state. Otherwise, the sleep state determining unit 24 determines that the subject is in a light sleep state.

As the first to the fifth determination thresholds, for example, two points of LF, HF, LF/HF, and a sum of standard derivatives of LF and HF at which a distribution concentration is high are selected. A middle point between the two points of LF/HF can be set as the first determination threshold (=the third determination threshold), a middle point between the two points of HF can be set as the second determination threshold (=the fourth determination threshold), and a middle point between the sum of the standard derivatives of LF and HF can be set as the fifth determination threshold.

If the middle point of the sum of the standard derivatives of LF and HF is smaller than the fifth determination threshold, and the HF is greater than the second determination threshold, then the sleep state determining unit 24 may determine that the subject is in a deep sleep state. Alternatively, if the LF/HF is smaller than the first determination threshold and the HF is smaller than the second determination threshold, then the sleep state determining unit 24 may determine that the subject is in a deep sleep state.

If the LF/HF is greater than the third determination threshold and the sum of the standard derivatives of LF and HF is greater than the fifth determination threshold, the sleep state determining unit 24 may determine that the subject is in a REM sleep state. Alternatively, if the LF/HF is greater than the third determination threshold, the sum of the standard derivatives of LF and HF is greater than the fifth determination threshold, and the average time interval in one cycle of the pulse wave is equal to or smaller than a sixth determination threshold, the sleep state determining unit 24 may determine that the subject is in a REM sleep state.

The sleep state determining unit 24 can change the first to the sixth determination thresholds in consideration of the influence of a circadian rhythm of the subject according to time. It is known that a fluctuation in the autonomic nervous system is influenced by a change in the sleep state and by a circadian rhythm of a living body. To lessen the influence, the sleep state determining apparatus 10 includes the time measuring unit 17, which changes the first to the sixth determination thresholds to correspond to the time. It is thereby possible to lessen the influence by circadian rhythm and improve sleep state determination accuracy.

The sleep state determining unit 24 calculates and displays a good sleep rate as represented by the following Equation 2 so as to generalize the sleep state based on determinations explained above. In the Equation 2, symbol abs denotes an operation symbol of an absolute value.

Good sleep rate(%)=[1−(constant A)×abs{(deep sleep rate)−(standard deep sleep rate)}/(standard deep sleep rate)−(constant B)×abs{(REM sleep rate)−(standard REM sleep rate)}/(standard REM sleep rate)]×100    (2)

Figure 8:
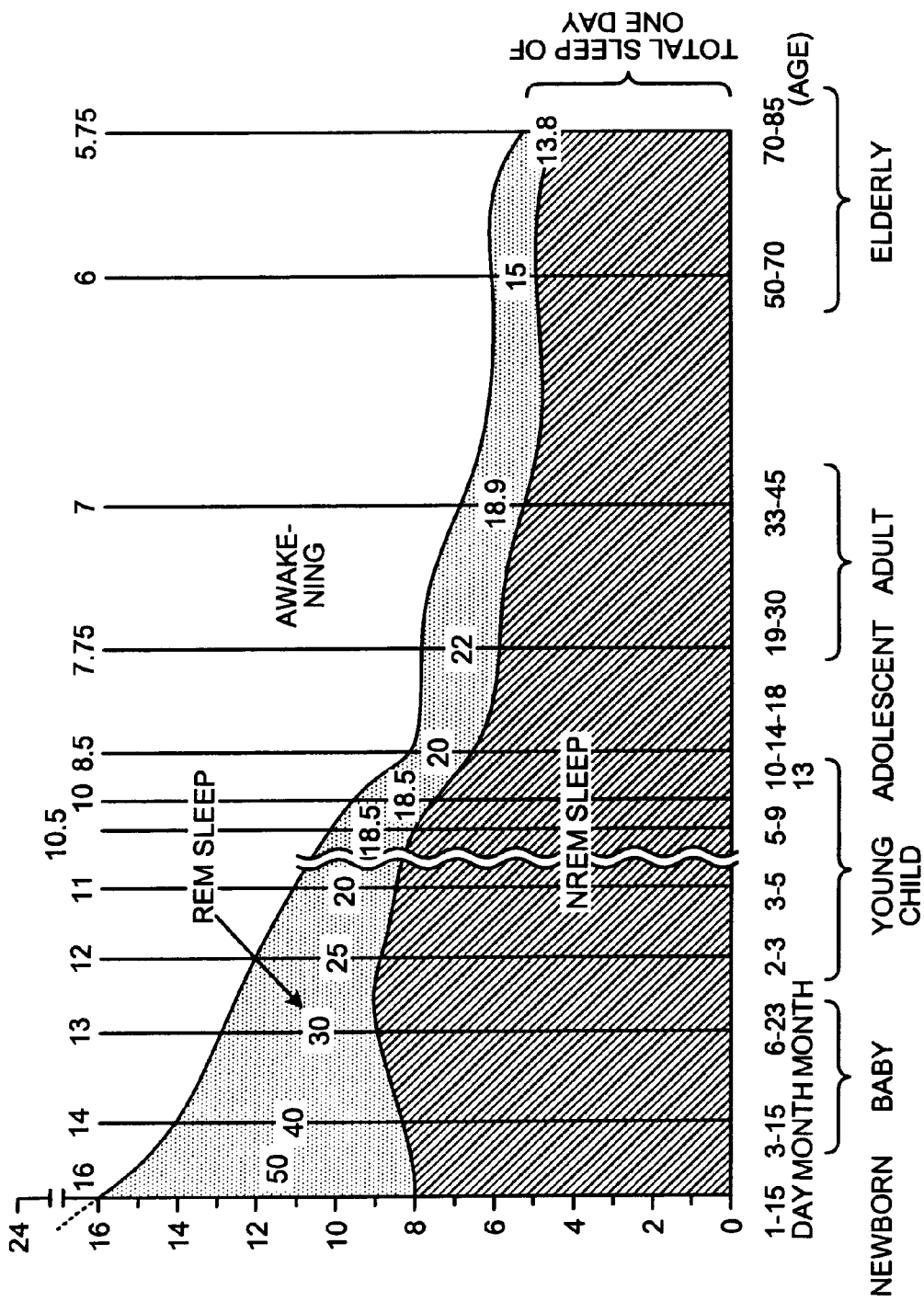
FIG. 8 is a standard deep sleep rate and a standard REM sleep rate indicated by Equation 2.

The standard deep sleep rate and the standard REM sleep rate shown in the Equation 2 will be explained with reference to FIG. 8. The standard deep sleep rate and the standard REM sleep rate are statistically known for each age and sex, therefore, these rates can be fixedly set based on the known rates. Since these rates also change according to a time zone or a time passage since sleep, a good sleep rate according to each time zone is acquired and an average good sleep rate can be calculated. In addition, average rates of past data on the subject can be used as the standard deep sleep rate and the standard REM sleep rate. Further, the body movement amount can be added, as a parameter, to calculate the good sleep rate.

An example of the display of a result of the sleep state determination made by the sleep state determining unit 24 shown in FIG. 1 will now be explained with reference to FIGS. 9 and 10.

Figure 9:
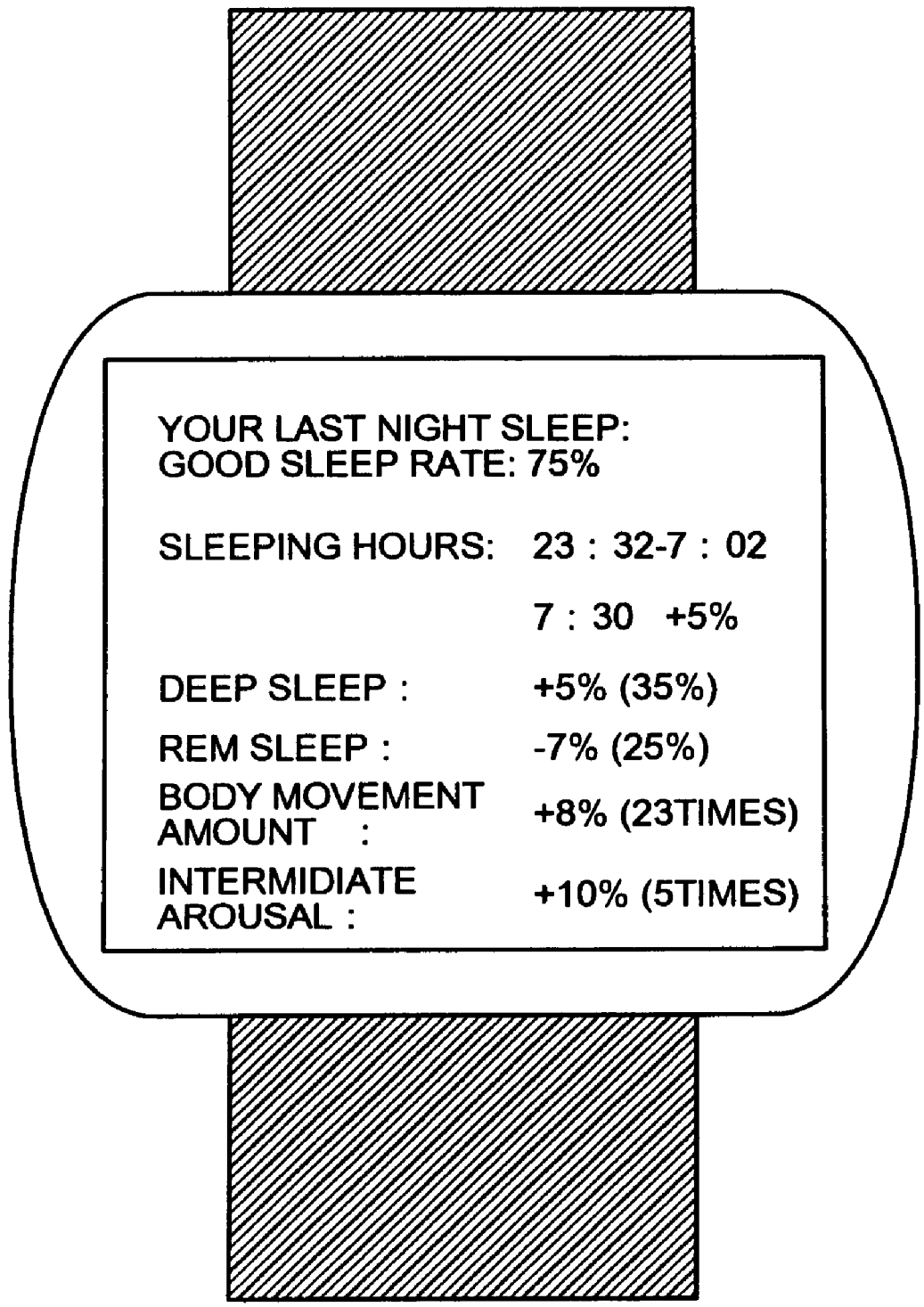
FIG. 9 is one example of displaying a result of a sleep state determination made by a sleep state determining unit.
Figure 10:
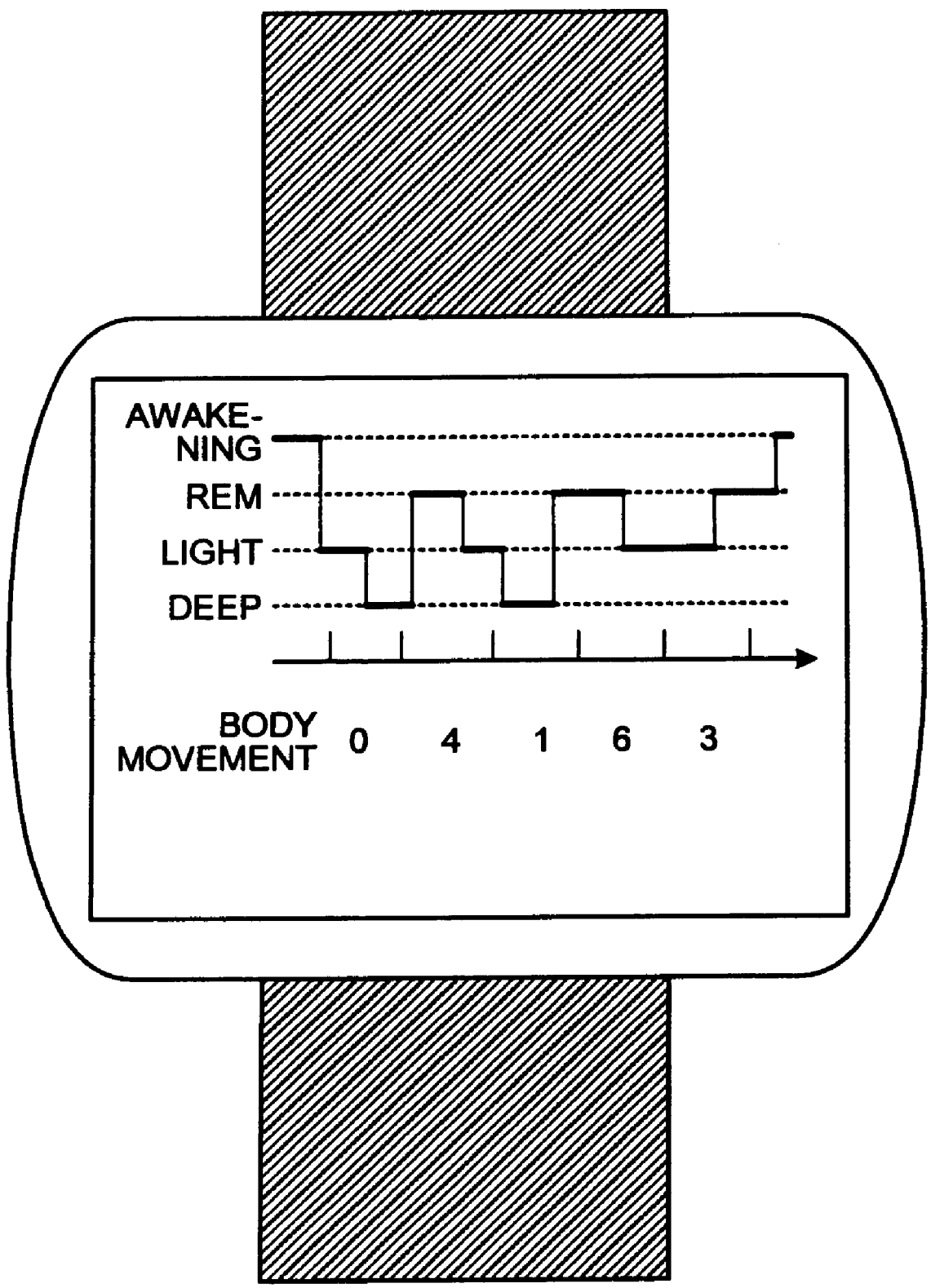
FIG. 10 is another example of displaying the result of the sleep state determination made by the sleep state determining unit.

As shown in FIG. 9, the sleep state determination result generalizes the sleep state by the good sleep rate and sleeping hours, and shows differences of the deep sleep rate, the REM sleep rate, the body movement rate, and the intermediate arousal rate from their respective standard rates. Namely, FIG. 9 shows that the deep sleep rate is higher by 5% from the standard deep sleep rate. In addition, 35% in parenthesis for the deep sleep indicates a rate of a deep sleep time in the sleeping hours of 7:30. As shown in FIG. 10, the sleep state determination result is displayed in the form of a graph in which body movement frequencies can be displayed for the respective time zones.

Referring back to FIG. 1, the controller 25 controls entirety of the sleep state determining apparatus 10. The controller 25 receives a request or an instruction of the subject, and controls a processing request and a data flow for each processor. Specifically, the controller 25 controls the processors to turn ON or OFF power, to start a sleep state determining function, to display the sleep state determination result and the like by a request of the subject.

Figure 11:
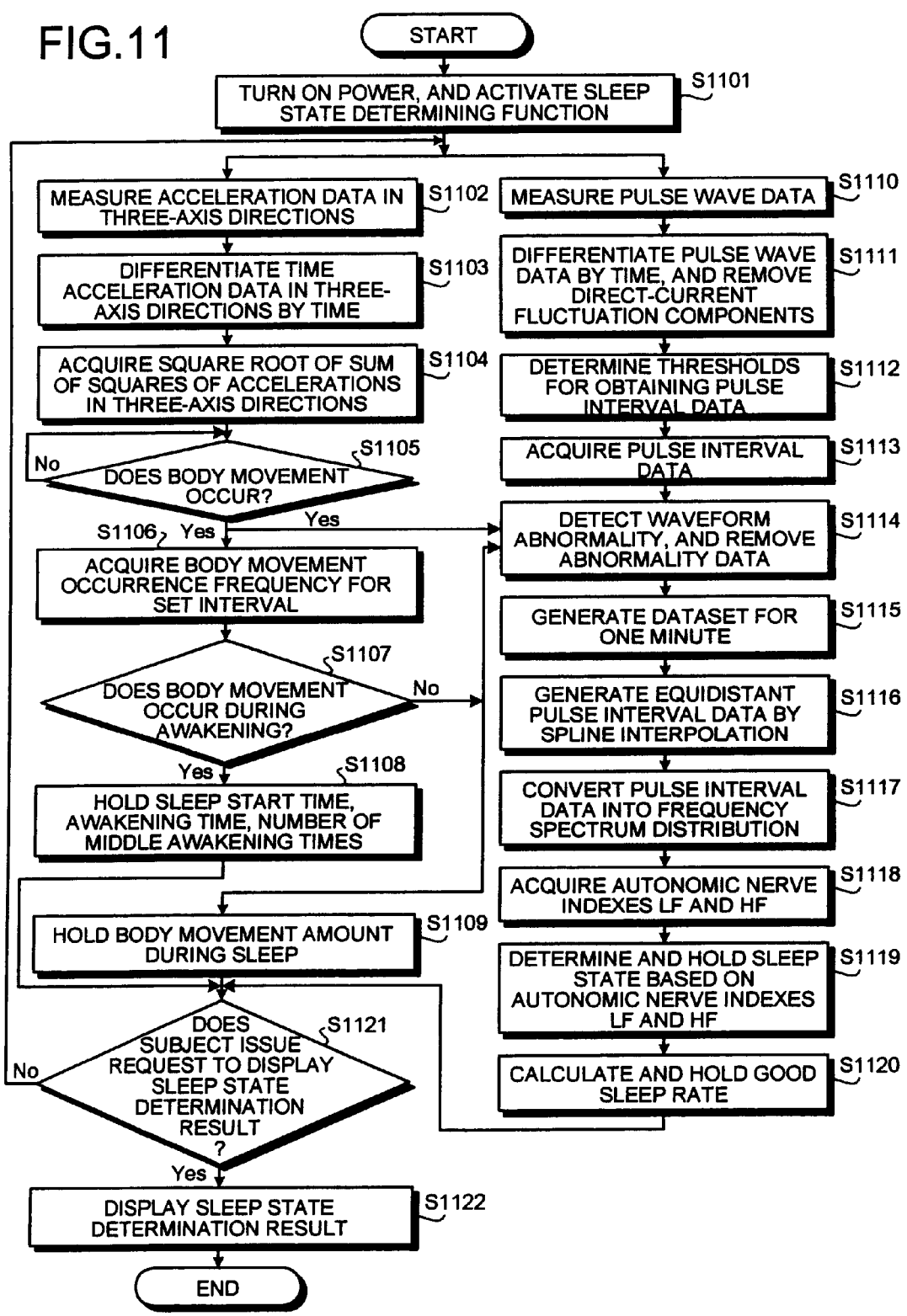
FIG. 11 is a flowchart of sleep state determination procedures performed by the sleep state determining apparatus.

Sleep state determination procedures performed by the sleep state determining apparatus 10 shown in FIG. 1 will be explained. FIG. 11 is a flowchart of the sleep state determination procedures. When the subject has the sleep state determining apparatus 10 attached before sleep, and the subject turns ON the power of the apparatus 10 and activates the sleep state determining function using the input unit 11 (at step S1101), the sleep state determining apparatus 10 starts measuring acceleration data and pulse wave data using the acceleration sensor 141 and the pulse wave sensor 151, respectively (at steps S1102 and S1110).

The body movement sampling data processor 20 differentiates the acceleration data in three-axis directions acquired from the body movement measuring unit 14 by time, and obtains differential coefficients of the accelerations in the three-axis directions (at step S1103). The body movement sampling data processor 20 obtains the square root of the sum of squares of the differential coefficients of the accelerations in the three-axis directions (at step S1104). The body movement determining unit 191 receives the square root of the sum of squares of the differential coefficients of the accelerations in the three-axis directions obtained by the body movement sampling data processor 20, and waits until a body movement occurs (at step S1105). Specifically, the body movement determining unit 191 determines that the body movement occurs if the fluctuation amount of the body movement data, which is the square root of the sum of squares of the differential coefficients of the accelerations in the three-axis obtained by the body movement sampling data processor 20, is greater than the first predetermined threshold. For example, as the first predetermined threshold, 0.01 G, which is a minimum minute body movement used in the body movement measuring instrument, is used.

If the body movement occurs ("YES" at step S1105), the body movement determining unit 191 notifies the waveform abnormality detector 221 of the occurrence of the body movement. If the body movement occurs ("YES" at step S1105), the awakening determining unit 192 acquires a body movement occurrence frequency for a set interval, for example, one minute (at step S1106), and determines whether the body movement occurs while the subject awakes (at step S1107). Specifically, the awakening determining unit 192 determines that the body movement occurs while the subject awakes if the body movement occurrence frequency determined by the body movement determining unit 191 is equal to or higher than the second predetermined threshold. The awakening determining unit 192 determines that the body movement occurs while the subject is in sleep if the body movement occurrence frequency is lower than the second predetermined threshold. For example, as the second predetermined threshold, the frequency of 20 times/minute is selected from among past body movement frequencies during awakening.

As a result, if the awakening determining unit 192 determines that the subject is in an awakening state ("YES" at step S1107), the awakening determining unit 192 causes the storage unit 13 to hold a sleep start time, an awakening time, a number of intermediate arousal times (at step S1108). If the awakening determining unit 192 determines that the body movement occurs during sleep ("NO" at step S1107), the awakening determining unit 192 notifies the waveform abnormality detector 211 that the body movement data determined as the body movement is a body movement during sleep. The awakening determining unit 192 causes the storage unit 13 to hold the body movement amount during sleep (at step S1109).

The pulse wave sampling data processor 21 samples pulse wave data from the pulse wave, differentiates the series of pulse wave data thus sampled by time, and removes the direct-current fluctuation components from the series of pulse wave data (at step S1111). The pulse wave sampling acquiring unit 21 acquires the maximum and the minimum pulse wave data within a predetermined time interval among the series of pulse wave data from which the direct-current fluctuation components are removed, and determines the predetermined value between the maximum and the minimum as the third predetermined threshold (at step S1112). For example, as the third predetermined threshold, the value having an amplitude of the difference between the maximum and the minimum that is 90% of the amplitude of the minimum is used. Further, periods of time when the series of pulse wave data coincident with the third predetermined threshold appear is calculated, from the series of pulse wave data from which the direct-current fluctuation components are removed, and the pulse interval data is acquired from the interval of the calculated periods of time (at step S1113).

The waveform abnormality detector 221 identifies the body movement during sleep from the body moment by notification of the body movement determining unit 191 and the awakening determining unit 192. If the fluctuation amount of the body movement data determined as the body movement during sleep, which body movement amount is an average in a pulse interval, is equal to or greater than the fifth predetermined threshold, the waveform abnormality detector 221 determines that the body movement amount is large, and detects the pulse interval data measured in parallel with the body movement data determined as the body movement during sleep as a waveform abnormality. Further, the abnormality data remover 222 removes the pulse interval data measured in parallel with the body movement data determined as the body movement during awakening and the pulse interval data detected as the waveform abnormality by the waveform abnormality detector 221 from the series of pulse interval data (at step S1114).

The pulse interval data processor 22 generates a data set for one minute using the series of pulse interval data, from which the waveform abnormality is removed by the abnormality data remover 222 (at step S1115). The pulse interval data interpolating unit 223 spline-interpolates the pulse interval data, from which the waveform abnormality is removed by the abnormality data remover 222, that is, interpolates the pulse interval data using the high-order polynomial, thereby generating equidistant pulse interval data (at step S1116).

The frequency spectrum converter 231 converts the series of pulse interval data processed by the pulse interval data processor 22 into the frequency spectrum distribution by the frequency analysis method such as the FFT method (at step S1117). The autonomic nerve index acquiring unit 232 acquires the autonomic nerve indexes LF and HF from a plurality of power spectra of the series of pulse interval data converted into the frequency spectrum distribution by the frequency spectrum converter 231 (at step S1118). Specifically, the autonomic nerve index acquiring unit 232 acquires the autonomic nerve indexes LF and HF by averaging the three points of the peak of the power spectra and two equidistant points before and after the peak.

The sleep state determining unit 24 determines the sleep state of the subject based on the autonomic nerve indexes LF and HF, and causes the storage unit 13 to hold the determination result (at step S1119). The sleep state determining unit 24 calculates the good sleep rate so as to generalize the sleep state of the subject, and causes the storage unit 13 to hold the calculated good sleep rate (at step S1120). The good sleep rate is automatically displayed during the awakening determination. The sleep state determining unit 24 also determines whether the subject issues a request to display the sleep state determination result (at step S1121). If the subject issues the sleep state determination result display request ("YES" at step S1121), the sleep state determining unit 24 displays the sleep state determination result held in the storage unit 13 in the displaying unit 12 according to the request of the subject (at step S1122). If the subject does not issues the request ("NO" at step S1121), then the processing returns to the step S1102, and the procedures up to the step S1120 are repeated.

Figure 12:
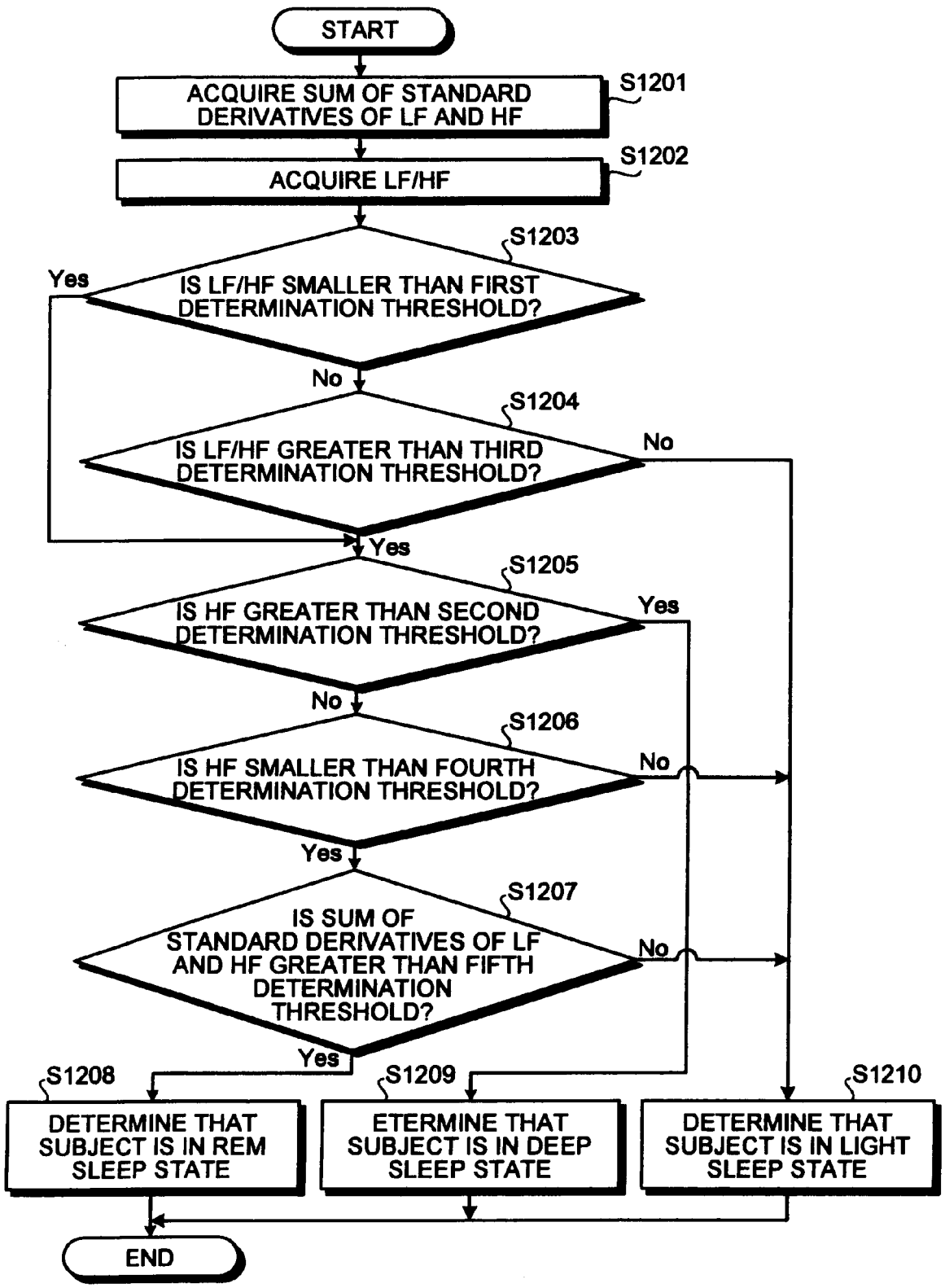
FIG. 12 is a flowchart of the sleep state determination procedures in more detail based on autonomic nerve indexes.

The sleep state determination procedures based on the autonomic nerve indexes LF and HF shown in FIG. 11 will be explained in more detail. FIG. 12 is a flowchart of the sleep state determination procedures in more detail based on the autonomic nerve indexes LF and HF. The sleep state determining unit 24 acquires the sum of the standard derivatives of the autonomic nerve indexes LF and HF for the sleep state determination (at step S1201), and acquires LF/HF (at step S1202).

The sleep state determining unit 24 determines whether the LF/HF is smaller than the first determination threshold (at step S1203). If the LF/HF is smaller than the first determination threshold ("YES" at step S1203), the sleep state determining unit 24 determines whether the HF is greater than the second determination threshold (at step S1205). If the HF is greater than the second determination threshold ("YES" at step S1205), the sleep state determining unit 24 determines that the subject is in a deep sleep state (at step S1209).

If the LF/HF is equal to or greater than the first determination threshold ("NO" at step S1203), the sleep state determining unit 24 determines whether the LF/HF is greater than the third determination threshold (at step S1204). If the LF/HF is greater than the third determination threshold ("YES" at step S1204), the sleep state determining unit 24 determines whether the HF is greater than the second determination threshold (at step S1205). If the HF is equal to or smaller than the second determination threshold ("NO" at step S1205), the sleep state determining unit 24 determines whether the HF is smaller than the fourth determination threshold (at step S1206). If the HF is smaller than the fourth determination threshold ("YES" at step S1206), the sleep state determining unit 24 determines whether the sum of the standard derivatives of the LF and HF is greater than the fifth determination threshold (at step S1207). If the sum of the standard derivatives of the LF and HF is greater than the fifth determination threshold ("YES" at step S1207), the sleep state determining unit 24 determines that the subject is in a REM sleep state (at step S1208).

If the LF/HF is equal to or smaller than the second determination threshold ("NO" at step S1204), if the HF is equal to or greater than the fourth determination threshold ("NO" at step S1206), or if the sum of the standard derivatives of the LF and HF is equal to or smaller than the fifth determination threshold ("NO" at step S1207), then the sleep state determining unit 24 determines that the subject is in a light sleep state (at step S1210).

As the first to the fifth determination thresholds, two points at which distribution concentration of each of the LF, HF, and LF/HF measured for a night for each subject is high are selected, for example. The middle point between the two points for the LF/HF can be set as the first determination threshold (=the third determination threshold), the middle point between the two points for the HF can be set as the second determination threshold (=the fourth determination threshold), and the middle point between the two points for the LF can be set as the fifth determination threshold.

As explained so far, according to the first embodiment, if the fluctuation in the body movement data is greater than the first predetermined threshold, it is determined that the body movement occurs. If it is determined that the body movement occurs, the series of pulse interval data, from which the pulse interval data measured in parallel with the body movement data determined as the body movement is removed, is processed. The sleep state is determined based on the autonomic nerve indexes acquired from the series of pulse interval data. Therefore, the influence of the body movement on the pulse wave and the influence of the pulse wave abnormality such as arrhythmia or apnea on the pulse wave can be lessened, and the sleep state determining accuracy can be thereby improved.

If it is determined that body movement occurs during sleep, the series of pulse interval data, from which the pulse interval data measured in parallel with the body movement data determined as the body movement is removed, is processed, and the sleep state is determined based on the autonomic nerve indexes acquired from the series of pulse interval data. Therefore, the influence of the body movement on the pulse wave and the influence of the pulse wave abnormality such as arrhythmia or apnea on the pulse wave can be lessened, and the sleep state determining accuracy can be thereby improved.

The series of pulse interval data, from which the pulse interval data measured in parallel with the body movement data determined as the body movement is removed, is interpolated using the high-order polynomial. Therefore, the series of pulse interval data which is non-equidistant since the abnormality data is removed from the data can be converted into the frequency spectrum distribution, and the autonomic nerve indexes necessary for the sleep state determination can be acquired. Therefore, the influence of the body movement on the pulse wave and the influence of the pulse wave abnormality such as arrhythmia or apnea on the pulse wave can be lessened, and the sleep state determining accuracy can be thereby improved.

Assume that the indexes LF and HF are the power spectrum in the low frequency region and the power spectrum in the high frequency region, respectively among the power spectra. If LF/HF is smaller than a first determination threshold and HF is greater than a second determination threshold, the sleep state determining unit 24 determines that the subject is in a deep sleep state. If the LF/HF is greater than a third determination threshold, the index HF is smaller than a fourth determination threshold, and a sum of standard derivatives of the indexes LF and HF is greater than a fifth determination threshold, then the sleep state determining unit 24 determines that the subject is in a REM sleep state. Otherwise, the sleep state determining unit 24 determines that the subject is in a light sleep state. Therefore, the influence of the body movement on the pulse wave and the influence of the pulse wave abnormality such as arrhythmia or apnea on the pulse wave can be lessened, and the sleep state determining accuracy can be thereby improved.

Since the acceleration data in the three-axis directions are measured as the body movement data, the body movement can be measured handy with high accuracy. Therefore, the influence of the body movement on the pulse wave and the influence of the pulse wave abnormality such as arrhythmia or apnea on the pulse wave can be lessened, and the sleep state determining accuracy can be thereby improved.

In the first embodiment, the instance in which the sleep state determining apparatus 10 lessens the influence of the body movement on the pulse wave sensor 151 using the acceleration sensor 141 is explained. However, the sleep state determining apparatus 10 can be also applied to detecting an abnormality such as arrhythmia or apnea during sleep. In a second embodiment, therefore, the instance in which the sleep state determining apparatus 10 detects an abnormality such as arrhythmia or apnea during sleep will be explained. It is noted that constituent elements common to the first and the second embodiments will not be explained herein.

Figure 13:
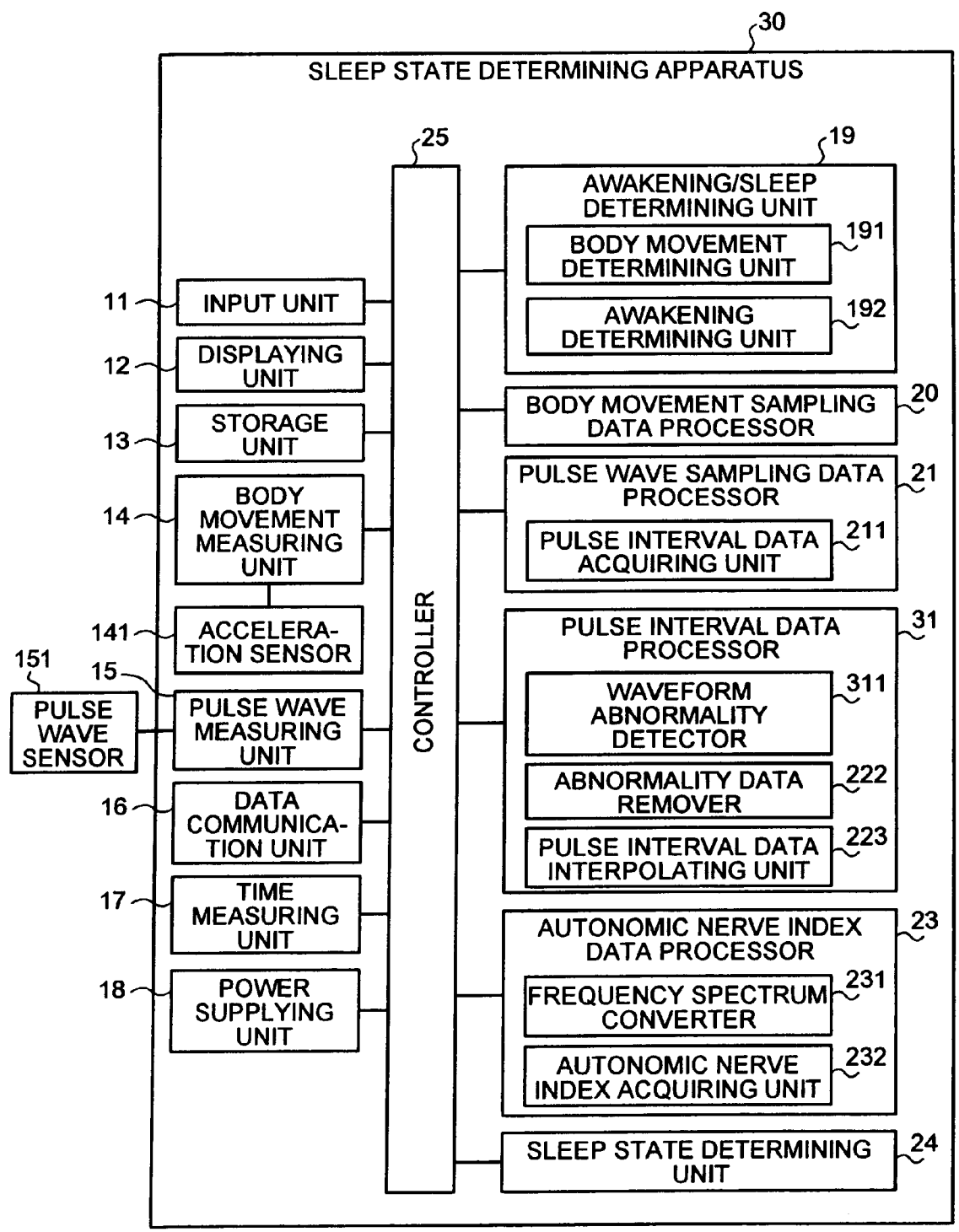
FIG. 13 is a functional block diagram of configuration of a sleep state determining apparatus according to a second embodiment of the present invention.

Configuration of the sleep state determining apparatus 30 according to the second embodiment will first be explained. FIG. 13 is a functional block diagram of the configuration of the sleep state determining apparatus 30 according to the second embodiment. The functional block diagram is equal in configuration to the functional block diagram according to the first embodiment shown in FIG. 1 except for the function of the waveform abnormality detector 311 of the pulse interval data processor 31.

The waveform abnormality detector 311 in the sleep state determining apparatus 30 according to the second embodiment is a processor that calculates a degree of coincidence between a waveform of the acquired pulse interval data and a waveform of normal pulse interval data, and that detects that the waveform of the acquired pulse interval data is abnormal if the coincidence degree is smaller than a fourth predetermined threshold. Specifically, the waveform abnormality detector 311 calculates a coefficient of a correlation between the waveform of the acquired pulse interval data and the waveform of the normal pulse interval data. If the correlation coefficient is smaller than the fourth predetermined threshold, the waveform abnormality detector 311 detects the waveform abnormality of the pulse interval data. As the fourth predetermined threshold, 0.5 is used, for example. The waveform abnormality detector 311 also makes a dynamic programming (DP) matching between the waveform of the acquired pulse interval data and a waveform of abnormal pulse interval data, and detects a waveform identification and an occurrence frequency. One example of a result of a sleep state determination made by the sleep state determining unit 24 shown in FIG. 13 will be explained with reference to FIGS. 14 and 15.

Figure 14:
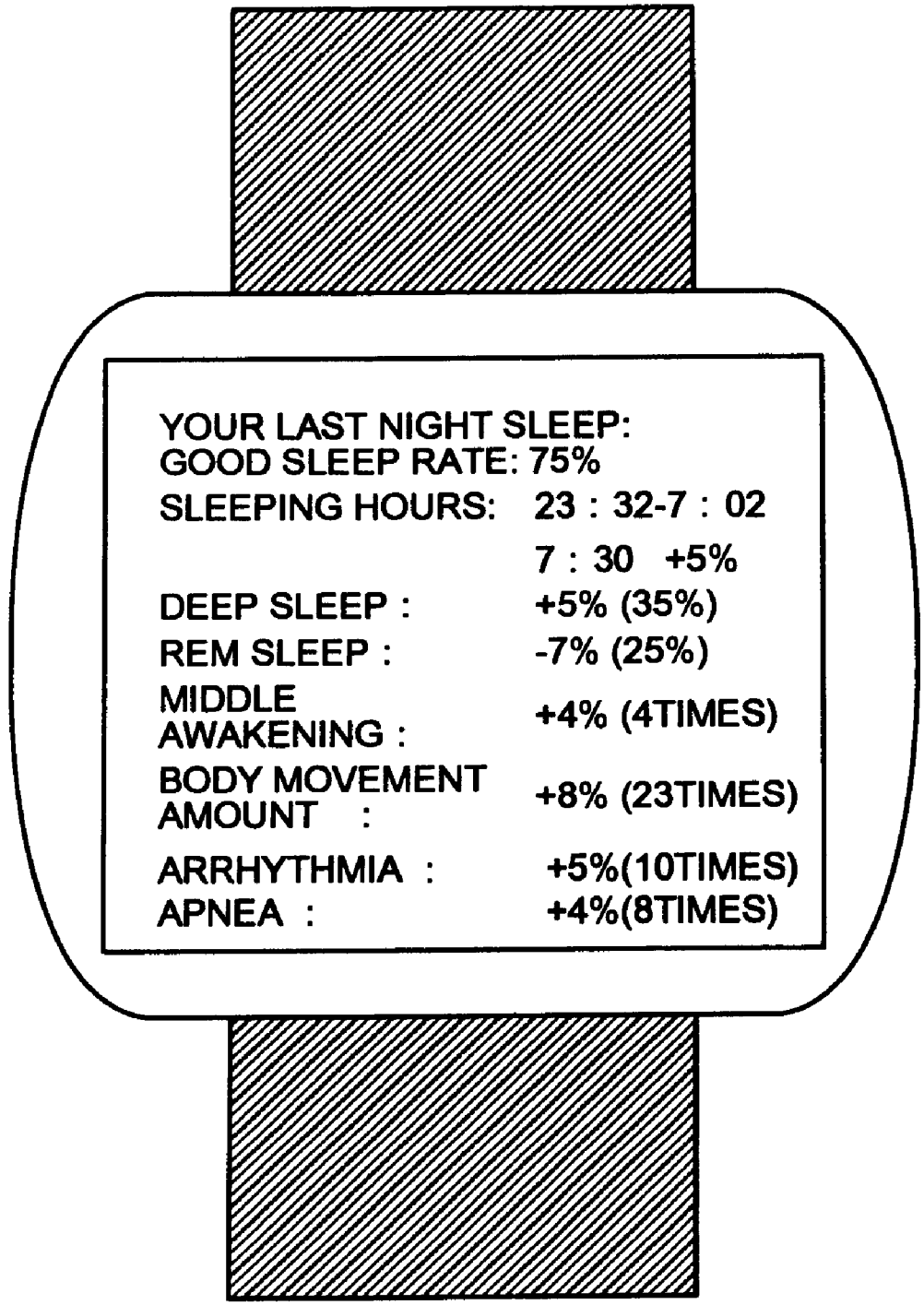
FIG. 14 is one example of a result of a sleep state determination made by a sleep state determining unit.
Figure 15:
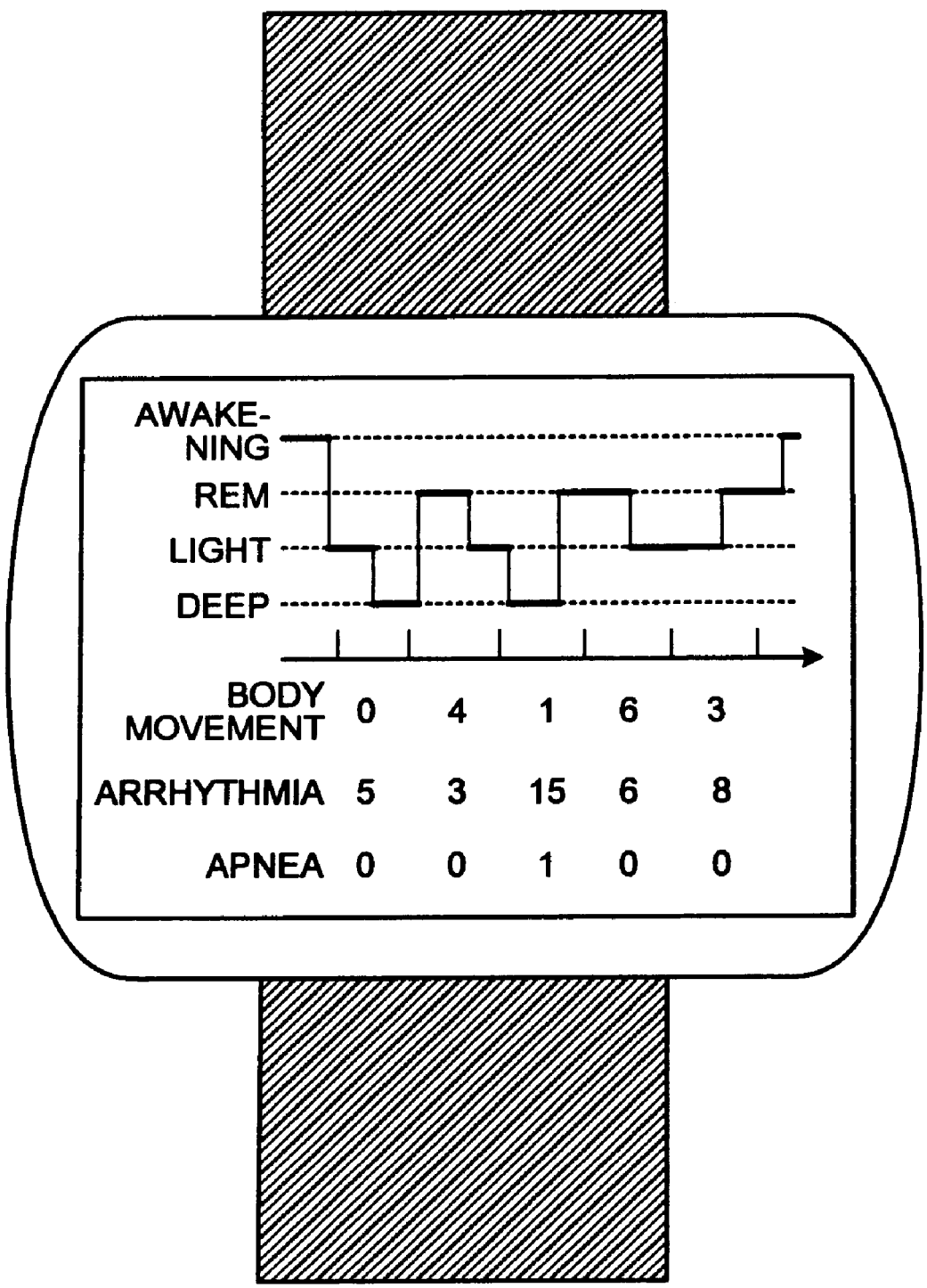
FIG. 15 is another example of the result of the sleep state determination made by the sleep state determining unit.

As shown in FIG. 14, an apnea rate and an arrhythmia rate are added to the sleep state determination result shown in FIG. 9. The result indicates the abnormality detected by the waveform abnormality detector 311. As shown in FIG. 15, the sleep state determination result can be displayed in the form of graphs for the sleep state of awakening, REM sleep, deep sleep, or light sleep, the body movement, the apnea frequency and the arrhythmia frequency for each time zone.

Figure 16:
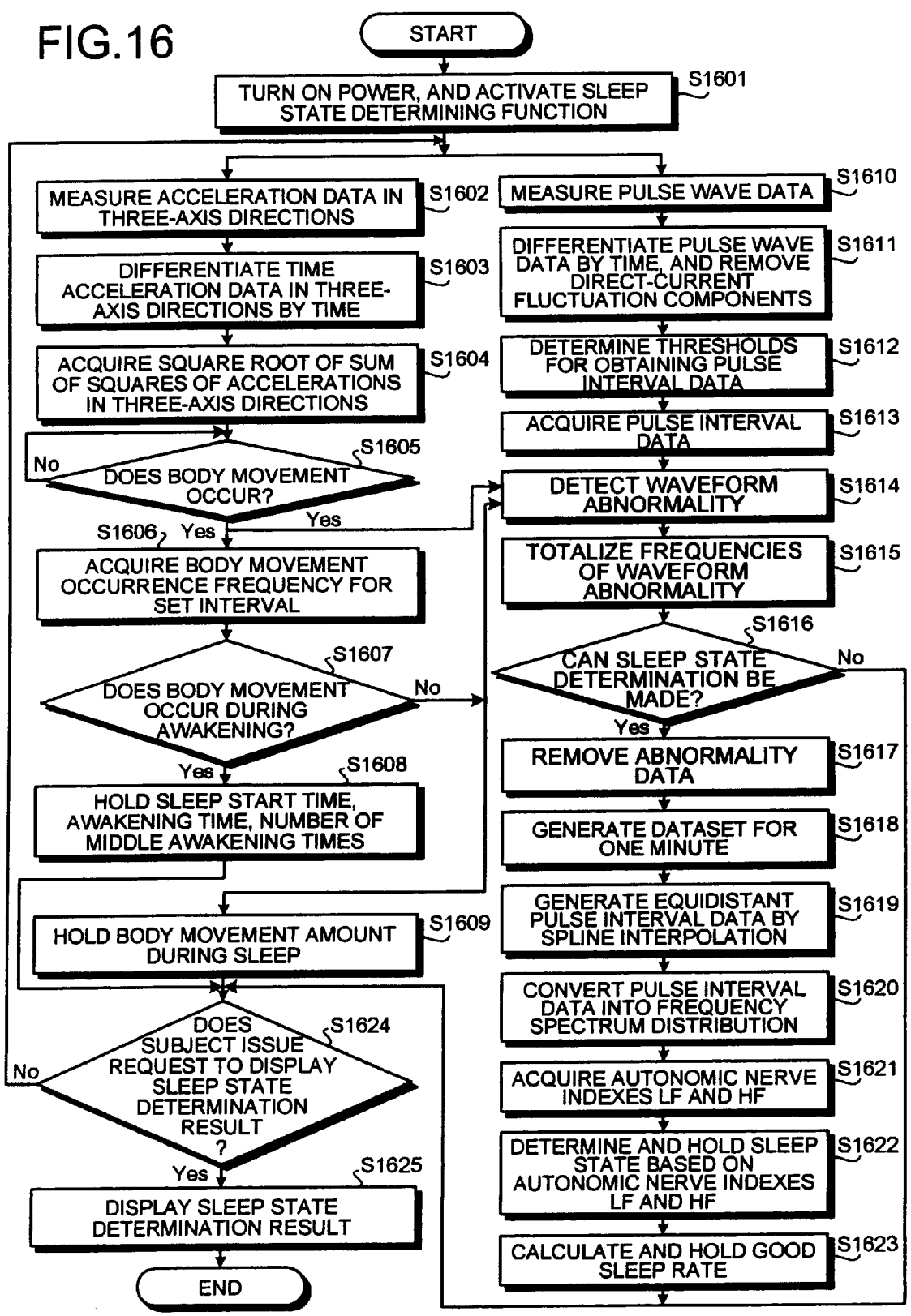
FIG. 16 is a flowchart of sleep state determination procedures performed by the sleep state determining apparatus.

Sleep state determination procedures performed by the sleep state determining apparatus 30 shown in FIG. 13 will be explained. FIG. 16 is a flowchart of the sleep state determination procedures. The procedures are equal to those according to the first embodiment except for steps S1614 to S1617. Therefore, only the steps S1614 to S1617 will be explained herein.

The waveform abnormality detector 311 calculates the coincidence degree between the waveform of the pulse interval data for which it is determined that the body movement occurs during sleep by the awakening determining unit 192 and the waveform of the normal pulse interval data. If the coincidence degree is smaller than the fourth predetermined threshold, the waveform abnormality detector 311 detects that the waveform of the acquired pulse interval data is abnormal (at step S1614). Specifically, the waveform abnormality detector 311 calculates the coefficient of the correlation between the waveform of the acquired pulse interval data for which it is determined that the body movement occurs during sleep by the awakening determining unit 192 and the waveform of the normal pulse interval data. If the correlation coefficient is smaller than the fourth predetermined threshold, the waveform abnormality detector 311 detects that the waveform abnormality occurs to the pulse interval data. As the fourth predetermined threshold, 0.5 is used, for example.

The waveform abnormality detector 311 makes a DP matching between the waveform of the pulse interval data determined as the body movement during sleep by the awakening determining unit 192 and the waveform of abnormal pulse interval data such as arrhythmia or apnea during sleep. The waveform abnormality detector 311 detects and calculates the waveform identification and the occurrence frequency of the waveform abnormality (at step S1615). The pulse interval data processor 31 acquires the occurrence frequency of the waveform abnormality detected by the waveform abnormality detector 311, and determines whether a sleep state determination can be made (at step S1616).

If the occurrence frequency of the waveform abnormality is high as a result, predetermined number of data cannot be secured, and the sleep state determination cannot be, therefore, made ("NO" at step S1616), the sleep state determining unit 24 determines that the body movement occurs or the waveform abnormality occurs (at step S1624). If the occurrence frequency of the waveform abnormality is low, the predetermined number of data can be secured, and the sleep state determination can be, therefore, made ("YES" at step S1616), and procedures at a step S1617 and the following are executed.

As explained so far, according to the second embodiment, the coincidence degree between the waveform of the pulse interval data determined as the body movement during sleep by the awakening determining unit 192 and the waveform of the normal pulse interval data is calculated. If the coincidence degree is smaller than the fourth predetermined threshold, the pulse interval data determined by the awakening determining unit 192 as the body movement during sleep is detected as the waveform abnormality. Therefore, the influence of the body movement on the pulse wave and the influence of the pulse wave abnormality such as arrhythmia or apnea on the pulse wave can be lessened, and the sleep state determining accuracy can be thereby improved.

The coefficient of the correlation between the waveform of the pulse interval data determined as the body movement during sleep by the awakening determining unit 192 and the waveform of the normal pulse interval data is calculated. If the correlation coefficient is smaller than the fourth predetermined threshold, the waveform of the pulse interval data determined as the body movement during sleep by the awakening determining unit 192 is detected as the waveform abnormality. Therefore, the influence of the body movement on the pulse wave and the influence of the pulse wave abnormality such as arrhythmia or apnea on the pulse wave can be lessened, and the sleep state determining accuracy can be thereby improved.

Further, the DP matching is made between the waveform of the pulse interval data determined as the body movement during sleep by the awakening determining unit 192 and the waveform of the abnormal pulse interval data, and the waveform identification and the occurrence frequency of the waveform abnormality are detected. Therefore, the influence of the body movement on the pulse wave and the influence of the pulse wave abnormality such as arrhythmia or apnea on the pulse wave can be lessened, and the sleep state determining accuracy can be thereby improved.

In the first and the second embodiments, the instance in which the sleep state determining apparatus 10, 30 employs, as the body movement sensor, the acceleration sensor 141 is explained. However, the sleep state determining apparatus can also employ, as the body movement sensor, a mat sensor. The instance in which the sleep state determining apparatus employs, as the body movement sensor, a mat sensor will be explained. It is noted that constituent elements common to the first and the third embodiments will not be explained herein.

Figure 17:
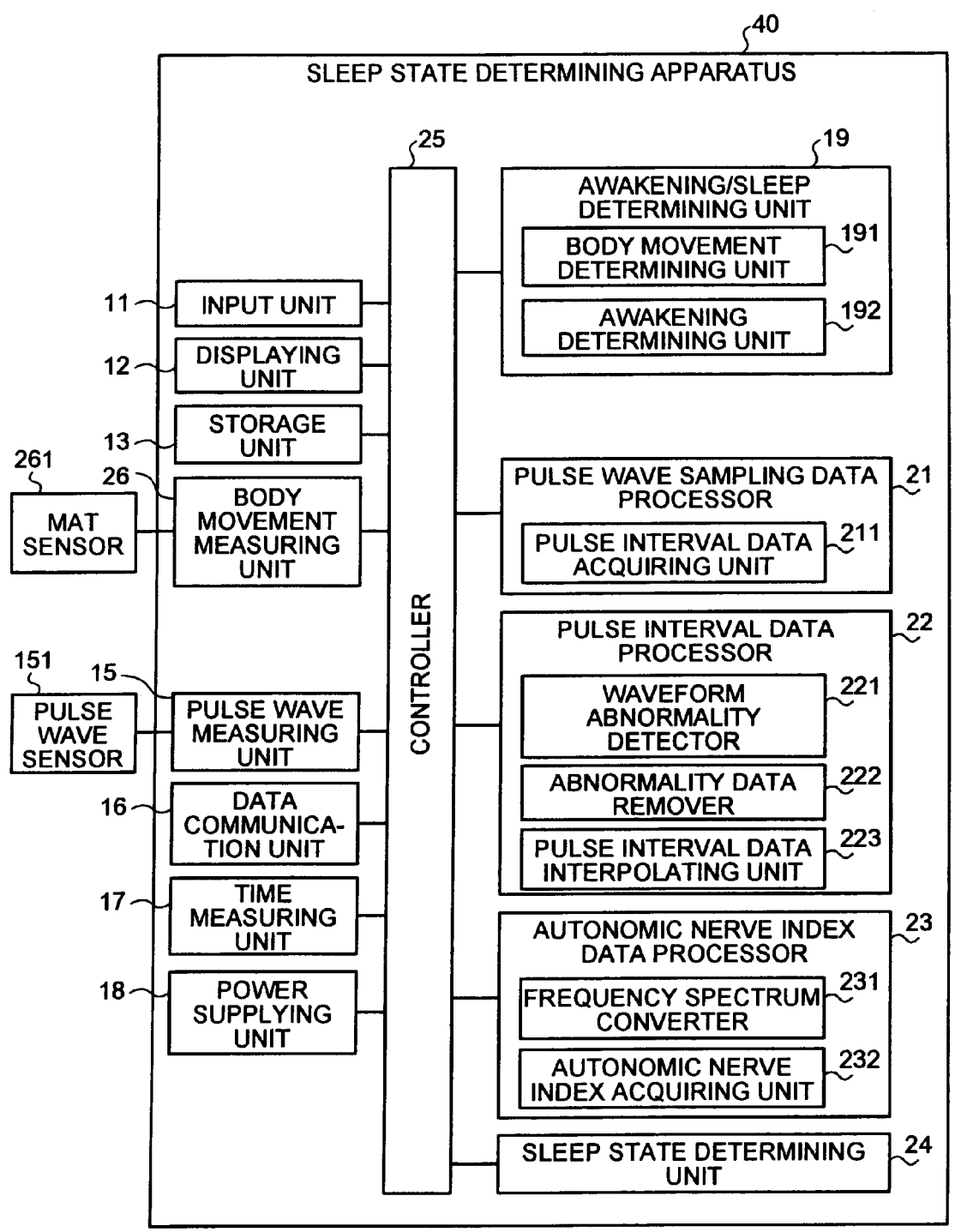
FIG. 17 is a functional block diagram of configuration of a sleep state determining apparatus according to a third embodiment of the present invention.
Figure 18:
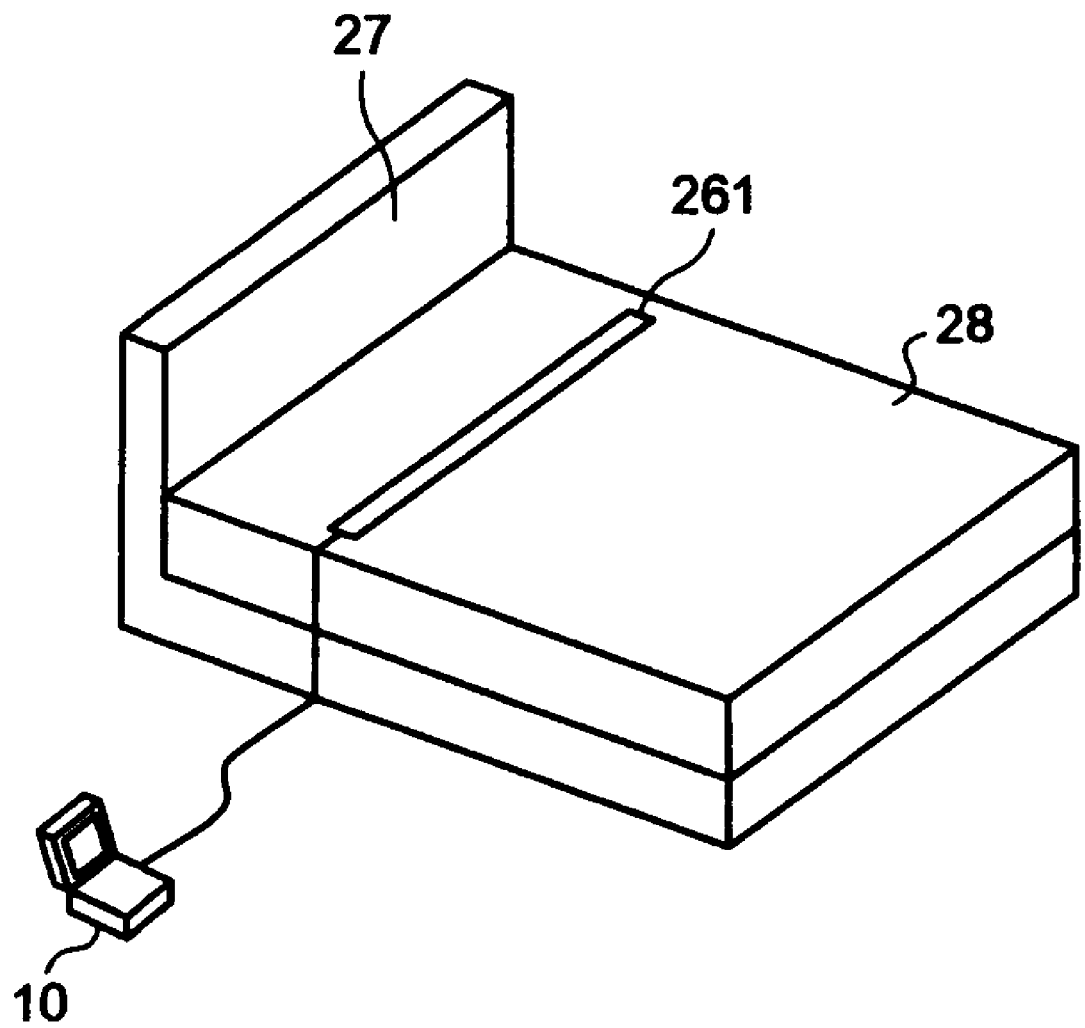
FIG. 18 is one example of arrangement of a mat sensor of the sleep state determining apparatus.

Configuration of the sleep state determining apparatus 40 according to the third embodiment will first be explained with reference to FIG. 17. The functional block diagram is equal in configuration to the functional block diagram according to the first embodiment shown in FIG. 1 except for a body movement measuring unit 26 and a mat sensor 261. The arrangement of the mat sensor in the sleep state determining apparatus 40 shown in FIG. 17 will be explained. FIG. 18 depicts one example of the arrangement of the mat sensor in the sleep state determining apparatus 40 shown in FIG. 17.

As shown in FIG. 18, the mat sensor 261 is provided on a surface of a mattress 28 of a bed 27, and detects an absence of the subject, a presence of the subject on bed, and a body movement. Specifically, the mat sensor 261 is a piezoelectric element obtained by forming a high polymer piezoelectric material such as polyvinylidene fluoride into a thin film, attaching flexible electrode films on both surfaces of the thin film, and forming the resultant film into a tape. The body movement measuring unit 26 converts an output signal of the mat sensor 261 into a digital quantity by an A/D converter via a filter and an amplifier.

The sleep state determining apparatus 40 according to the third embodiment can determine the sleep state of the subject in the same processing procedures as those according to the first and the second embodiments after the body movement measuring unit 26 converts the output signal of the mat sensor 261 into the digital quantity. The sleep state determining apparatus 10, 30 according to each of the first and the second embodiments employs, as the body movement sensor, the acceleration sensor 141. However, the body movement sensor according to the present invention is not limited to the acceleration sensor 141 but the other body movement sensor such as the mat sensor 261 can be employed.

Figure 19:
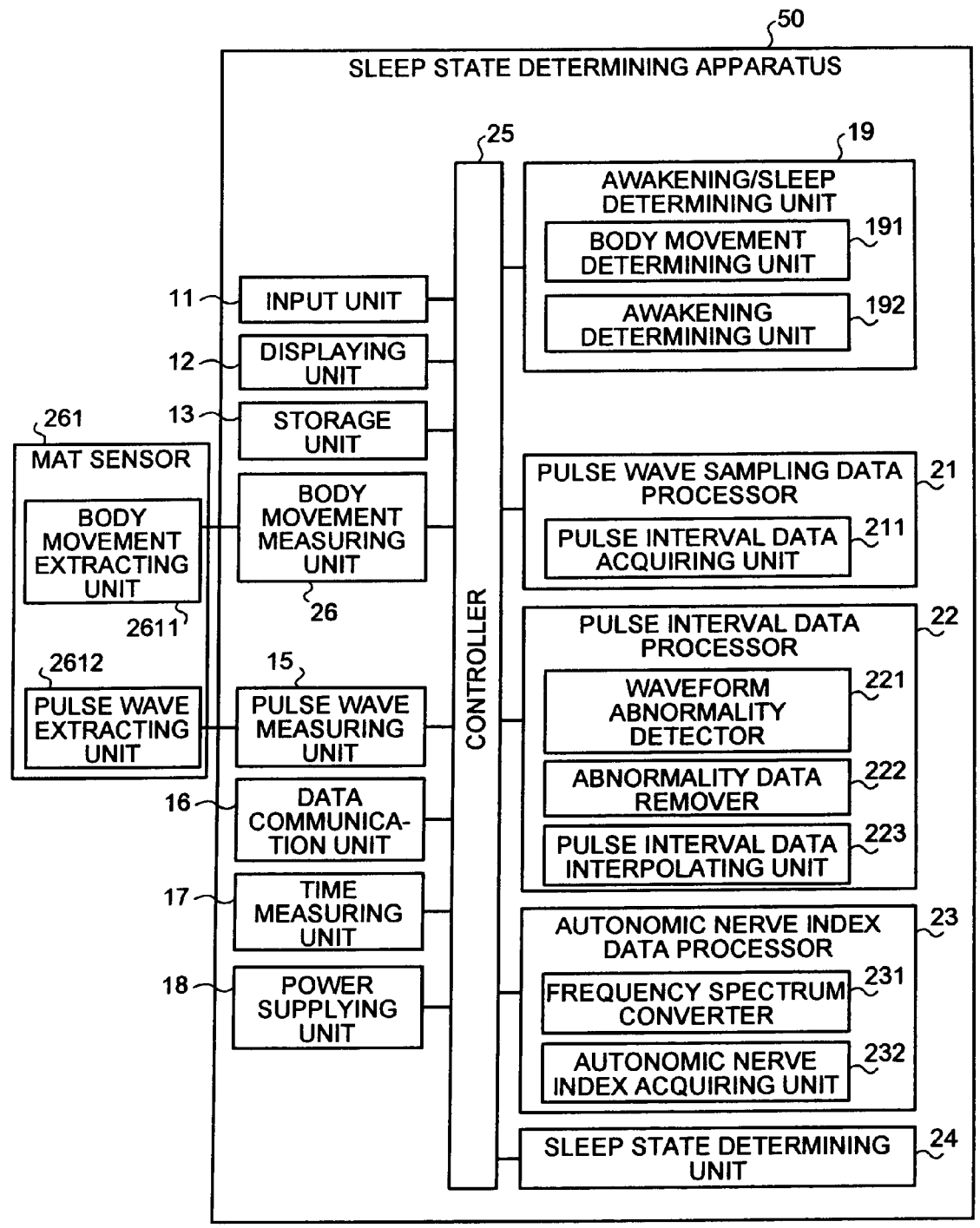
FIG. 19 is a functional block diagram of configuration of a sleep state determining apparatus according to a fourth embodiment of the present invention.

Referring to FIG. 19, configuration of the sleep state determining apparatus 50 according to a fourth embodiment will be explained. FIG. 19 is a functional block diagram of the configuration of the sleep state determining apparatus 50 according to the fourth embodiment. The configuration of the sleep state determining apparatus 50 in which a body movement extracting unit 2611 and a pulse wave extracting unit 2612 are provided in the mat sensor 261 can be applied to the present invention. The body movement extracting unit 2611 extracts a body movement component from the sensor that is provided on the surface of the mattress 28 of the bed 27 and that detects the body movement and the like, as explained. The pulse wave extracting unit 2612 extracts a pulse wave component from an output of the mat sensor by a frequency analysis or the like. The extracted body movement component and pulse wave component are input to the body movement measuring unit 26 and the pulse wave measuring unit 15, respectively, and the sleep state is determined in the same processing procedures as those according to the first and the second embodiments.

According to the embodiments explained above, if the fluctuation in the body movement data is greater than the first predetermined threshold, it is determined that the body movement occurs. If it is determined that the body movement occurs, the series of pulse interval data, from which the pulse interval data measured in parallel with the body movement data, for which it is determined that the body movement occurs, is removed, is processed. The sleep state is determined based on the autonomic nerve indexes acquired from the series of data-processed pulse interval data. Therefore, the influence of the body movement on the pulse wave and the influence of the pulse wave abnormality such as arrhythmia or apnea on the pulse wave can be lessened, and the sleep state determining accuracy can be thereby improved.

What is claimed is:

1. A biotic sleep state determining apparatus that determines a sleep state of a subject based on a series of pulse interval data that indicate a time interval of one cycle of a pulse wave of the subject, and on body movement data that indicates a body movement of the subject, the apparatus comprising:

a body movement determining unit configured to determine that the body movement occurs if a fluctuation amount of the body movement data is greater than a first predetermined threshold;

a pulse interval data processor that processes the series of pulse interval data, after removing pulse interval data measured in parallel with the body movement data from the series of pulse interval data, if the body movement determining unit determines that the body movement occurs, and thereafter processes the series of pulse interval data other than the removed pulse interval data;

a sleep state determining unit configured to determine the sleep state based on autonomic nerve indexes acquired from the series of pulse interval data processed by the pulse interval data processor;

an awakening determining unit configured to determine that the body movement occurs during awakening if an occurrence frequency of the body movement determined by the body movement determining unit is equal to or greater than a second predetermined threshold, and to determine that the body movement occurs during sleep if the occurrence frequency of the body movement is smaller than the second predetermined threshold, wherein the pulse interval data processor that processes the series of pulse interval data after removing the pulse interval data measured in parallel with the body movement data, determined as the body movement during sleep from the series of pulse interval data, if the awakening determining unit determines that the body movement occurs during sleep;

an abnormality data remover that removes the pulse interval data measured in parallel with the body movement data determined as the body movement by the awakening determining unit from the series of pulse interval data, if the awakening determining unit determines that the body movement occurs, and the pulse interval data processor that processes the series of pulse interval data after the abnormality data remover removes the pulse interval data measured in parallel with the body movement data determined as the body movement from the series of pulse interval data;

a pulse interval data interpolating unit configured to interpolate the series of pulse interval data, from which the abnormality data remover removes the pulse interval data measured in parallel with the body movement data determined as the body movement, wherein the pulse interval data processor processes the series of pulse interval data temporally equidistant based on the series of pulse interval data interpolated by the pulse interval data interpolating unit;

a body movement measuring unit configured to measure acceleration data in three-axis directions as the body movement data; and a body movement sampling data processor that differentiates the acceleration data in the three-axis directions measured by the body movement measuring unit by time, that obtains differential coefficients of the acceleration data in the three-axis directions, and that calculates a fluctuation amount of the body movement data, the fluctuation amount of the body movement data being a square root of a sum of squares of the differential coefficients of the acceleration data in the three-axis directions, wherein the body movement determining unit is configured to determine that the body movement occurs if the fluctuation amount of the body movement data calculated by the body movement sampling data processor is greater than the first predetermined threshold.

2. A biotic sleep state determining method of determining a sleep state of a subject based on a series of pulse interval data that indicate a time interval of one cycle of a pulse wave of the subject, and on body movement data that indicates a body movement of the subject, the method comprising:

determining that the body movement occurs if a fluctuation amount of the body movement data is greater than a first predetermined threshold;

processing the series of pulse interval data after removing pulse interval data measured in parallel with the body movement data from the series of pulse interval data, if the body movement occurs;

determining the sleep state based on autonomic nerve indexes acquired from the series of pulse interval data processed;

determining that the body movement occurs during awakening if an occurrence frequency of the body movement determined is equal to or greater than a second predetermined threshold, and determining that the body movement occurs during sleep if the occurrence frequency of the body movement is smaller than the second predetermined threshold, wherein the processing includes processing the series of pulse interval data after removing the pulse interval data measured in parallel with the body movement data determined as the body movement during sleep from the series of pulse interval data, if the body movement occurs during sleep;

removing the pulse interval data measured in parallel with the body movement data determined as the body movement from the series of pulse interval data, if the body movement occurs, and the series of pulse interval data is processed after removing the pulse interval data measured in parallel with the body movement data determined as the body movement from the series of pulse interval data; and interpolating the series of pulse interval data, from which the pulse interval data measured in parallel with the body movement data determined as the body movement is removed, wherein the processing includes processing the series of pulse interval data temporally equidistant based on the series of pulse interval data interpolated.

3. The method according to claim 2, further comprising:
converting the series of pulse interval data interpolated into a frequency spectrum distribution, and acquiring autonomic nerve indexes from a plurality of power spectra of the series of pulse interval data converted into the frequency spectrum distribution, wherein the determining includes determining the sleep state based on the autonomic nerve indexes acquired.

4. The method according to claim 3, wherein the determining includes determining that the subject is in a deep sleep state if LF/HF is smaller than a first determination threshold and HF is greater than a second determination threshold, determining that the subject is in a rapid eye movement REM sleep state if the LF/HF is grater than a third determination threshold, the HF is smaller than a fourth determination threshold, and a sum of standard derivatives of the LF and the HF is greater than a fifth determination threshold, and otherwise determining that the subject is in a light sleep state, in which the LF is a power spectrum in a low-frequency region and the HF is a power spectrum in a high-frequency region among the power spectra.

5. The method according to claim 4, further comprising:
measuring a time, wherein the determining includes changing the first to the fifth determination thresholds in consideration of an influence of a circadian rhythm of the subject according to the time measured.

* * * * *